United States Patent
Jennische et al.

(12) 
(10) Patent No.: US 9,962,424 B2
(45) Date of Patent: *May 8, 2018

(54) USE OF ANTISECRETORY FACTORS (AF) FOR OPTIMIZING CELLULAR UPTAKE

(71) Applicant: LANTMANNEN AS-FAKTOR AB, Stockholm (SE)

(72) Inventors: Eva Jennische, Gothenburg (SE); Stefan Lange, Gothenburg (SE); Hans-Arne Hansson, Hovas (SE)

(73) Assignee: LANTMÄNNEN AS-FAKTOR AB, Stockholm (SE)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/883,734

(22) Filed: Oct. 15, 2015

(65) Prior Publication Data

US 2016/0030515 A1 Feb. 4, 2016

Related U.S. Application Data

(63) Continuation of application No. 13/148,878, filed as application No. PCT/SE2010/050165 on Feb. 11, 2010, now Pat. No. 9,220,750, and a continuation-in-part of application No. 12/289,389, filed on Oct. 27, 2008, now Pat. No. 8,309,513, which is a continuation of application No. PCT/SE2007/000413, filed on Apr. 27, 2007.

(30) Foreign Application Priority Data

Feb. 11, 2009 (SE) ........................ 0900170

(51) Int. Cl.
| | |
|---|---|
| A61K 38/17 | (2006.01) |
| A61K 31/704 | (2006.01) |
| A61K 35/57 | (2015.01) |
| A61K 45/06 | (2006.01) |
| C07K 7/04 | (2006.01) |

(52) U.S. Cl.
CPC ........ *A61K 38/1709* (2013.01); *A61K 31/704* (2013.01); *A61K 35/57* (2013.01); *A61K 45/06* (2013.01); *C07K 7/04* (2013.01); *G01N 2333/912* (2013.01); *G01N 2500/10* (2013.01)

(58) Field of Classification Search
None
See application file for complete search history.

(56) References Cited

U.S. PATENT DOCUMENTS

| 8,389,468 B2 * | 3/2013 | Hansson | A61K 38/1709 |
| | | | 514/19.3 |
| 9,220,750 B2 * | 12/2015 | Jennische | A61K 38/1709 |
| 2002/0055457 A1 * | 5/2002 | Janus | A61K 31/00 |
| | | | 514/1 |
| 2005/0063979 A1 * | 3/2005 | Pickl | A61K 39/0005 |
| | | | 424/184.1 |
| 2008/0025524 A1 | 10/2008 | Petricoin et al. | |
| 2012/0093716 A1 | 4/2012 | Jennische et al. | |

FOREIGN PATENT DOCUMENTS

| CA | 1337590 | * 11/1995 | A61K 31/71 |
| WO | WO1997033909 | * 9/1997 | C07K 14/17 |
| WO | WO98/21978 A1 | 5/1998 | |
| WO | WO03/087840 A2 | 10/2003 | |
| WO | WO2005/030246 A1 | 4/2005 | |
| WO | WO2007/126363 A2 | 11/2007 | |
| WO | WO2007/126364 A2 | 11/2007 | |
| WO | WO2007/126365 A2 | 11/2007 | |
| WO | WO2008/069608 A1 | 6/2008 | |

OTHER PUBLICATIONS

Laurenius et al. Antisecretory factor counteracts secretory diarrhoea of endocrine origin. Clinical Nutrition (2003) 22(6): 549-552.*
Johansson et al. Molecular cloning and expression of a pituitary gland protein modulating intestinal fluid secretion. J Biol Chem. Sep. 1, 1995;270(35):20615-20.*
Wallgren, A. B., et al., "AF-16 Peptide Derived From the Endogenous Protein Antisecretory Factor, Decreases Tumor Interstitial Fluid Pressure," International Journal of Molecular Medicine, 24 (2009), Abstract.
Lange, S., "The AF Protein A Clinical Innovation of Endogenous Origin," Clinical Studies and Case reports, pp. 1-16, Aug. 2004.
Supplementary European Search Report issued in EP 10 74 1487.

* cited by examiner

*Primary Examiner* — Satyanarayana R Gudibande
*Assistant Examiner* — Jia-Hai Lee
(74) *Attorney, Agent, or Firm* — Cermak Nakajima & McGowan LLP; Malcolm K. McGowan

(57) ABSTRACT

The present invention relates to the use of an antisecretory factor (AF) protein, peptide, derivative, homologue, and/or fragment thereof, having equivalent functional activity, and/or a pharmaceutically active salt thereof, for optimizing delivery and cellular uptake of a pharmaceutical substance and/or formulation, or a gene delivery. Typically, said pharmaceutical substance and/or formulation comprises an anti-cancer drug, radiation therapy, an antibiotic substance, an antiviral substance or a drug targeting posttraumatic injury, neurodegeneration, a parasite, or an inflammatory condition.

10 Claims, 5 Drawing Sheets

USE OF ANTISECRETORY FACTORS (AF) FOR OPTIMIZING CELLULAR UPTAKE

CONTINUING APPLICATION DATA

Figure 1:
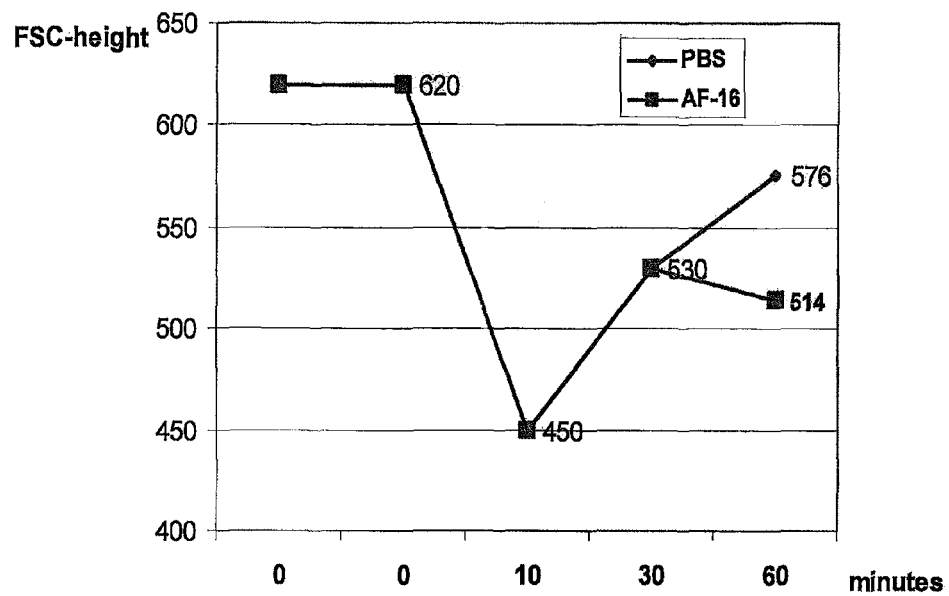
Figure 1:
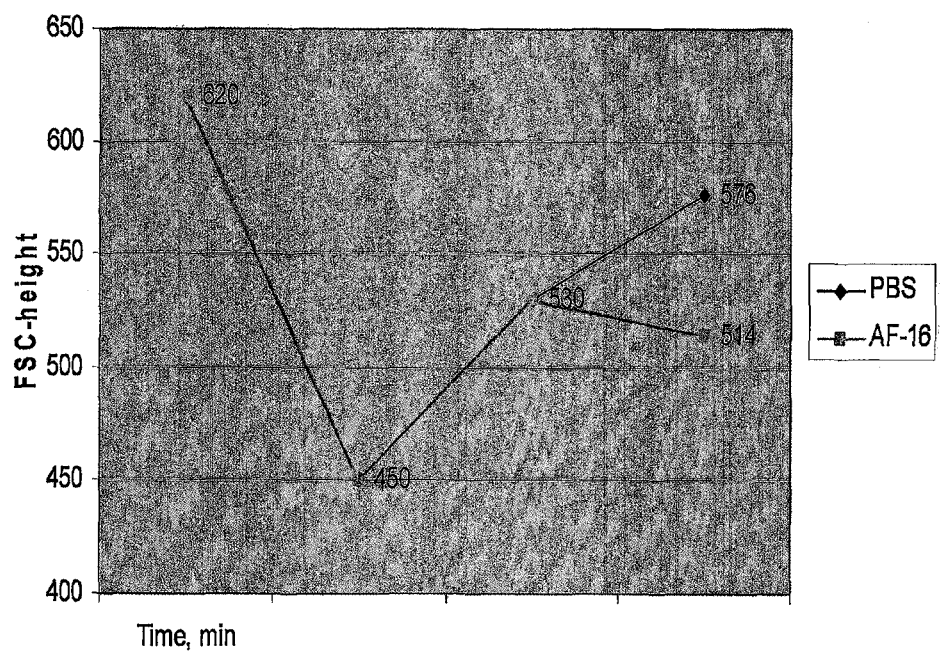

This application is a continuation of copending U.S. application Ser. No. 13/148,878, filed 10 Aug. 2011, which is national stage entry under 35 USC 371 of PCT/SE2010/050165, filed 11 Feb. 2010, claiming priority from Swedish application 0900170-2, filed 11 Feb. 2009, and a continuation-in-part of U.S. application Ser. No. 12/289,389, filed 27 Oct. 2008, now U.S. Pat. No. 8,309,513, which is a continuation of PCT/2007/000413, filed 27 Apr. 2007. The contents of these prior applications are incorporated herein in their entirety by reference.

FIELD OF INVENTION

The present invention relates to the use of an antisecretory factor (AF) protein, peptide, derivative, homologue, and/or fragment thereof, having equivalent functional activity, and/or a pharmaceutically active salt thereof, for optimizing delivery and cellular uptake of a pharmaceutical substance and/or formulation, or a gene delivery. Typically, said pharmaceutical substance and/or formulation comprises an anticancer drug, radiation therapy, an antibiotic substance, an antiviral substance or a drug targeting sequels of posttraumatic brain injuries, neurodegeneration, a parasite, or an inflammatory condition.

In general, the present invention relates to the surprising insight that antisecretory factor (AF) actively influences the equilibrium between phosphorylated and dephosphorylated states of a vast number of functional proteins and that it in particular can intervene in the biological activation of trans-membrane proteins, such as $Na^+$—$K^+$-$2Cl^-$ co-transporter (NKCC1), by interacting with CAP/ponsin (c-Cbl associated protein) and FAK (focal adhesion kinase). AF can thus effectively regulate and/or normalize abnormal activity of said ion channel in perturbed and/or pathological cells, thereby effectively normalizing the intracellular pressure in the pathological cell, potentially allowing an improved cellular uptake of a pharmaceutical substance, such as a drug used in e.g. cancer, Inflammation, or trauma therapy, or a nucleic acid sequence used for gene delivery.

The present invention further of course also relates to the use of the above described surprising insight that antisecretory factor (AF) protein as well as a peptide derived thereof comprising the essential consensus sequence of AF can intervene in the biological activation of transmembrane proteins and/or in particular co-transporters, such as NKCC1, through CAP/ponsin and FAK in a broad variety of methods for improved drug design, for screening for and/or evaluating potential AF inhibitory and/or enhancing substances, and for evaluating efficacy and/or verifying functional activity of a new or known antisecretory factor (AF) protein, peptide, derivative, homologue, and/or fragment thereof, having equivalent functional activity, and/or a pharmaceutically active salt thereof.

In another aspect, the newfound insight of AF's biological cellular function further enables the design of a new and reliable diagnostic and/or prognostic tool for monitoring and/or verifying and/or enhancing the therapeutic control of a cancer and/or abnormal tissue growth or activity in a subject suffering e.g. from cancer.

BACKGROUND OF THE INVENTION

Defective regulation of cell secretion underlies the clinical manifestations of a number of important human diseases ranging from cystic fibrosis to secretory diarrhea and brain edema.

The regulation of metazoic cells' dimensions and internal milieu is a very high priority matter for their normal function, multiplication and survival. The cytoskeleton, formed by the fairly static microtubules and intermediate filaments, and the dynamic actin filament network act as sensors of cells' shape, dimensions, three dimensional shape and mechanical load. Excessive inflow of water and ions increase a cell's dimensions, e.g., as occurring if the cell is exposed to a hypotonic extracellular environment. In contrast, a hypertonic extracellular milieu renders the cell to shrink. Any divergence from the normal status of a cell is immediately and forcefully counteracted as a cell, for the sake of its survival and optimal function, is giving its highest priority to maintain a "normal" status. Thereby, the actin filaments and associated myosin 1 form a sensing system alarming on any divergence from the normal conditions. The actin filaments are attached to lipid rafts and caveolae, as well as to junctional complexes and desmosomes/hemidesmosomes and to other constituents of the cytoskeleton, microtubules and intermediate filaments, thereby being able to read the condition prevalent in a cell. The actin filament system is linked to protein complexes at the cytoplasmic face of lipid rafts and caveolae, which arrangement enables the actin filaments to monitor the effectors' parts of the cell. Thereby the signals emitted by the actin filaments induce counteractions, enabling the cell to maintain its normal status. These actin linked proteins are e.g. galectin, filamin and flotillin, and they often form oligomers. The flotillin-1 and flotillin-2 form oligomers, mostly tetramers, which are anchoring lipid rafts to the actin filament network. Flotillin-1 binds with very high affinity to the AF protein as well as to the AF-derived peptide AF-16, while flotillin-2 is firmly linking actin filaments. The level of flotillin-1 is rapidly adjusted by degradation of free flotillin-1, rendering dynamics to the system. It is known that flotillins monitor certain kinases and phosphatases, which in turn regulate the activity of transmembrane proteins, e.g. ion pumps and G-protein linked systems such as NKCC's, the activity of which are further linked to the levels and activities of CAP/ponsin and FAK.

Optimization of drug and gene delivery is a topic of great interest. The optimization can be achieved via site-specific and targeted delivery, controlled drug release, and by finding ways to deliver higher concentrations of a drug into tissues of interest despite various barriers. Targeted delivery can serve to lower the required drug dose and minimize toxic side effects, which is e.g. crucial for the success of cancer treatment by immunotherapy, chemotherapy and/or radiation. Controlled release of drugs can be advantageous in the management of chronic diseases such as trauma-related conditions, neurodegenerative diseases, diabetes and hypertension.

Chemotherapy and immunotherapy are therapeutic approaches of major importance for the treatment of both localized and metastasized tumors. Since anticancer drugs are neither specific nor targeted to the cancer cells, improved delivery of anticancer drugs to tumor tissues in humans appears to be a reasonable, beneficial and achievable challenge. Scientists are working to increase the availability of drug for tumor uptake by 1) delaying the release preparations for long-lasting actions; 2) using liposome-entrapped drugs for prolonged effect or reduced toxicity; 3) administrating inert, non-toxic prodrugs for specific activation at the tumor site; 4) delivering antibody-mediated drugs; or 5) conjugating site-specific carriers to direct the drug to the tumor target. The latter depends heavily on pharmacokinetic investigations. Some success has been achieved in enhancing the efficacy and reducing the toxicity of drugs.

What is more, it is generally known in the field that the response of tumor to various anticancer drugs is tumor-size dependent in many aspects. In general, problems stem partly from the fact that the entire tumor cell populations do not respond equally to a certain treatment. As a result of recent progress in cancer biology, it has become evident that cellular heterogeneity of the tumor underlies the difficulties of treating primary and metastatic tumors with chemotherapy. Moreover, as tumors grow, marked diversity develops on the tissue level as well. An uneven distribution with an increase of areas of lower growth fraction and of poorer drug delivery is more distinct in larger tumors. Heterogeneous distribution and low levels of tumor blood flow are considered to be causally related to the heterogeneous nature of tumor tissue. Considering the lack of evidence of a lymphatic system within the tumor, increased interstitial fluid pressure may be a natural result that further impedes blood flow in the tumor.

The efficacy in cancer treatment of novel therapeutic agents such as monoclonal antibodies, cytokines and effector cells has been limited by their inability to reach their target in vivo in adequate quantities. Molecular and cellular biology of neoplastic cells alone has failed to explain the non-uniform uptake of these agents. This is not surprising, since a solid tumor in vivo is not just a collection of cancer cells. In fact, it consists of two extracellular compartments: vascular and interstitial. Since no blood-borne molecule or cell can reach cancer cells without passing through these compartments, the vascular and interstitial physiology of tumors has received considerable attention in recent years. Three physiological factors responsible for the poor localization of macromolecules in tumors have been identified: (i) heterogeneous blood supply, (ii) elevated interstitial pressure, and (iii) long transport distances. The first factor limits the delivery of blood-borne agents to well-perfused regions of a tumor; the second factor reduces extravasations of fluid, nutrients, oxygen and macromolecules in the high interstitial pressure regions and also leads to an experimentally verifiable, radial outward convection in the tumor periphery which opposes the inward diffusion. The third factor increases the time required for slowly moving macromolecules, nutrients, or oxygen to reach distant regions of a tumor. Binding of any molecule to e.g. an antigen further lowers the effective diffusion rate by reducing the concentration of mobile molecules. Although the effector cells are capable of active migration, peculiarities of the tumor vasculature and interstitium may also be responsible for poor delivery of lymphokine activated killer cells and tumor infiltrating immuno active cells in solid tumors. Due to micro- and macroscopic heterogeneities in tumors, the relative magnitude of each of these physiological barriers would vary from one location to another and from one day to the next in the same tumor, and from one tumor to another. If genetically engineered macromolecules and effector cells, as well as low molecular weight cytotoxic agents, are to fulfill their clinical promise, strategies must be developed to overcome or exploit these barriers.

Solid tumors, enclosed by a capsule and sometimes divided by septa, often develop high interstitial fluid pressure (IFP) as a result of increased fluid leakage and impaired blood circulation and lymphatic drainage, as well as changes in the extracellular matrix composition and elasticity. This means that the arteriolar blood pressure at many occasions causes the IFP to reach high levels. Also swelling of tumor cells contributes to the raised IFP. Raised interstitial fluid pressure forms a barrier to drug delivery and hence, resistance to therapy.

A cell undergoes genetic and epigenetic changes during its transition to malignancy. Malignant transformation is also accompanied by a progressive loss of tissue homeostasis and perturbations in tissue architecture that ultimately culminates in tumor cell invasion of the parenchyma and metastatic spread to distant tissue and organ sites. Increasingly, cancer biologists have begun to recognize that a critical component of this transformation journey involves marked alterations in the mechanical phenotype of the cell and its surrounding microenvironment. These include modifications in cell and tissue structure, adaptive force-induced changes in the environment, altered processing of micromechanical cues encoded in the extracellular matrix (ECM), and cell-directed remodeling of the extracellular stroma. Solid tumors are commonly stiffer than normal tissue, and tumors have altered integrins.

Growing evidence indicates that critical steps in cancer progression such as cell adhesion, migration, and cell cycle progression are in parts regulated by the composition and organization of the microenvironment. The adhesion of cancer cells to components of the microenvironment and the forces transmitted to the cells via the actin network and the signaling complexes organized at focal adhesions, lipid rafts and caveolae, allow cancer cells to sense the local topography of the extracellular matrix and respond efficiently to growth and migration promoting cues.

The cytoskeleton, including its actin network, is known to be of crucial importance for the structure and function of normal, inflammatory and neoplastic cells. At e.g. a brain trauma, the cytoskeleton is extensively deranged at locations and to an extent varying with the applied forces. The actin filaments are as well disintegrating at encephalitis (Jennische et al., 2008) and at cholera toxin induced diarrhea (Hansson et al., 1984). Thus, the crucial roles of the cytoskeleton for the maintenance of normal dimensions of cells and for the emergence of dysfunctions are established.

Much attention has focused on the role of membrane chloride ($Cl^-$) channels in the maintenance of normal cell functions, emerging evidence highlights the importance of the $Na^+$—$K^+$-$2Cl^-$ co-transporter (NKCC) as an independent regulatory site that may determine the overall rate of cell secretion. The co-transporter NKCC1 is expressed in virtually all mammalian cells, where it plays a more generalized role in cell volume homeostasis, cell ionic composition, and, possibly, the control of cell growth. Emerging molecular evidence indicates that NKCC1 function is regulated in the short and long term at the level of protein phosphorylation, membrane targeting, and gene expression (Mathews, 2002). Thus, an improved understanding of the interactions between the cytoskeleton, flotillin oligomers, lipid rafts and effectors such as NKCC1 has lead the present inventors to new therapeutic approaches to cancer and to neurodegeneration, as well as to the treatment of a range of clinical conditions in which the cell dimensions and ion composition are disturbed.

The Na—K—Cl co-transporters are a class of membrane proteins that transport $Na^+$, $K^+$, and $Cl^-$ ions into and out of a wide variety of epithelial and non-epithelial cells. The transport process mediated by Na—K—Cl co-transporters is characterized by electro neutrality (almost always with stochiometry of 1Na:1K:2Cl) and inhibition by the "loop" diuretics such as bumetanide, benzmetanide, and furosemide. Presently, two distinct Na—K—Cl co-transporter isoforms have been identified by cDNA cloning and expression; genes encoding these two isoforms are located on different chromosomes and their gene products share approximately 60% amino acid sequence identity.

The NKCC1 (CCC1, BSC2) isoform is present in a wide variety of tissues. Most normal epithelial cells containing NKCC1 are secretory epithelia with the Na—K—Cl co-transporter localized to the basolateral membrane. By contrast, NKCC2 (CCC2, BSC1) is found only in the kidney, localized to the apical membrane of the epithelial cells of the thick ascending limb of Henle's loop and of the macula densa. Mutations in the NKCC2 gene result in Bartter's syndrome, an inherited disease characterized by hypo potassium metabolic alkalosis, hypercalciuria, salt wasting, and volume depletion. The two Na—K—Cl co-transporter isoforms are also part of a superfamily of cation-chloride co-transporters, which includes electroneutral K—Cl and Na—Cl co-transporters. Cancer cells, which mostly are apolar, do express high levels of NKCC, resulting in that the tumor cells in fact are swollen, i.e. having increased dimensions. Tumor cells have less precisely regulated ion pump and water channel systems, but still show a strong tendency to maintain their internal homeostasis. That means that the increased dimensions of tumor cells, enclosed by a capsule, contribute to the raise of the IFP common in solid tumors.

Na—K—Cl co-transporter activity is affected by a large variety of hormonal stimuli as well as by changes in cell volume. In many tissues this regulation (particularly of the NKCC1 isoform) is regulated by the balance between phosphorylation and dephosphorylation of regulatory systems, controlling the ion pumps prevalent in the lipid rafts through the specific protein kinases or phosphatases. (Haas, 1998)

Cell shrinkage-induced activation of NKCC involves an interaction between the cytoskeleton and protein phosphorylation events via PKC and myosin light chain kinase (MLCK). Osmotic control of Cl— secretion across the epithelium includes: (i) hyperosmotic shrinkage activation of NKCC1 via PKC, MLCK, p38, OSR1 and SPAK; (ii) deactivation of NKCC by hypotonic cell swelling and a protein phosphatase, and (iii) a protein tyrosine kinase acting on the focal adhesion kinase (FAK) to set levels of NKCC activity. The CAP component is interposed as well and takes parts in the step wise regulation of the extent of phosphorylation of NKCC, which determines its function within the lipid rafts (Hoffmann 2007).

At the electron microscopic level, a unique combination of integrin β1, the phosphorylated form of FAK at tyrosine 407 (pY407) and Na(+), K(+), 2Cl(−) co-transporter (NKCC1) were all co-localized only on the basolateral membrane in normal cells. The three proteins were also co-immunoprecipitated with each other in isotonic conditions, suggesting an osmosensing complex involving the three proteins. Only FAK pY407 was sensitive to hypotonic shock and became dephosphorylated with hypotonic shock, while FAK pY576 in the apical membrane and pY861 in cell-cell adhesions were insensitive to hypotonicity. It has been reported that chloride cells respond to hypotonic shock using integrin β1 as an osmosensor that is connected to dephosphorylation of FAK pY407 which leads to NKCC1 deactivation in the basolateral membrane and the inhibition of NaCl secretion by these epithelial cells (Marshall, 2008). Again, tumor cells commonly are apolar and thus the ion pumps in the lipid rafts are localized all along the cell surface, as apical and basolateral areas are not prevalent.

Thus, the same kind of ion pump is prevalent in normal cells as in cancer cells and in either case similarly monitored, albeit their localizations differ.

Integrins are cell surface receptors which, in part, mediate the adhesion of cells to the extracellular matrix. In addition to providing molecular "glue" essential for tissue organization and survival, integrins serve as dynamic signaling molecules. Integrins allow normal, non-transformed cells to sense that they are adhered to the extracellular matrix, thus providing a cell survival signal. This signal allows cells to proliferate in the presence of growth factors and in some instances prevents apoptosis. Integrins also mediate cell migration as it occurs in normal processes, such as angiogenesis, wound healing, repair of damage, monitor immune system function, and development. Aberrances in the expression and function of integrins contribute to many diseases and disorders, including cancer.

Focal adhesion kinase (FAK) is a non-receptor tyrosine kinase that is overexpressed in a variety of cancers and plays an important role in cell adhesion, migration, and anchorage-dependent growth (Tilgham, 2007)

Focal adhesion kinase (FAK), prevalent in practically all normal cells, is overexpressed in invasive and metastatic colon, breast, thyroid, and prostate cancers. Enhanced FAK immunostaining is detected in small populations of preinvasive (carcinoma in situ) oral cancers and in large populations of cells in invasive oral cancers. It has been hypothesized that FAK is probably not a classical oncogene but may be involved in the progression of cancer to invasion and metastasis. It is further hypothesized that overexpression of FAK in subpopulations of tumor cells leads to populations of cells with a high propensity toward invasion and metastasis (Kornberg, 1998).

Focal adhesion kinase (FAK) localizes to cellular focal adhesions or cell contacts within the extracellular matrix. FAK is activated by a variety of cell surface receptors and transmits signals to a range of targets. FAK participates in growth factor receptor-mediated signaling pathways and plays essential roles in cell survival, proliferation, migration, and invasion.

Overexpression of FAK is widely observed in numerous tumor types, and is used as a marker for invasion and metastasis. FAK could be therapeutically targeted at various levels, such as at the level of FAK gene transcription by regulating its transcription factor(s) with siRNA, at the FAK mRNA level with FAK siRNA, or at the protein level. At the protein level, FAK's localization to lipid rafts in focal adhesions could be disrupted by expression of dominant-negative FAK-Related Non-Kinase or its focal adhesion targeting domain, and its kinase activity could be inhibited by FIP200, the FAK kinase domain-interacting protein and kinase-activity inhibitor. In recent years, research has been focused on developing small molecule inhibitors against FAK transcription and activation, to provide additional approaches for potential tumor therapies (Lis. 2008).

Another substrate involved in the phosphorylation of intracellular substrates regulating the transduction and control of signals determining the level of activity of ion pumps is CAP, which is an adapter protein for the Cbl proto-oncogene product. CAP is acting as a link in the signaling pathway at the cytoplasmic leaflet of lipid rafts between flotillin and FAK. CAP is also known under the name ponsin. The name reflects that this factor originally was isolated and identified in over-expressing tumors and therefore named proto-oncogene product, but has subsequently been disclosed to be prevalent as well in normal cells.

Antisecretory factor is a 41 kDa protein that originally was described to provide protection against diarrhea diseases and intestinal inflammation (for a review, see Lange and Lönnroth, 2001). The antisecretory factor (AF) protein has been sequenced and its cDNA cloned. The antisecretory activity seems to be mainly exerted by a peptide located between the amino acid positions 35 and 50 on the antisecretory factor (AF) protein sequence and comprising at least 4-16, such as 4, 6, 8 or 16 amino acids of the consensus sequence. Immunochemical and immunohistochemical investigations have revealed that the antisecretory factor (AF) protein is present and may also be synthesized by most tissues and organs in a body. Synthetic peptides, comprising the antidiarrhoeic sequence, have prior been characterized (WO 97/08202; WO 05/030246). Antisecretory factor (AF) proteins and peptides have previously been disclosed to normalize pathological fluid transport and/or inflammatory reactions, such as in the intestine and the choroid plexus in the central nervous system after challenge with the cholera toxin (WO 97/08202). Food and feed with the capacity to either induce endogenous synthesis of AF or uptake of added AF have therefore been suggested to be useful for the treatment of edema, diarrhea, dehydration and inflammation in WO 97/08202. WO 98/21978 discloses the use of products having enzymatic activity for the production of a food that induces the formation of antisecretory factor (AF) proteins. WO 00/038535 further discloses the food products enriched in antisecretory factor (AF) proteins as such.

Antisecretory factor (AF) proteins and fragments thereof have also been shown to improve the repair of nervous tissue, and proliferation, apoptosis, differentiation, and/or migration of stem and progenitor cells and cells derived thereof in the treatment of conditions associated with loss and/or gain of cells (WO 05/030246) and to be equally effective in the treatment and/or prevention of intraocular hypertension (WO 07/126364), as for the treatment and/or prevention of compartment syndrome (WO 07/126363).

What is more, the present inventors recently showed that antisecretory factors were able to monitor and/or beneficially affect the structure, distribution and multiple functions of lipid rafts, receptors and/or caveolae in membranes and could thus be employed for the treatment and/or prevention of structural disorganization and dysfunction of lipid rafts and/or caveolae in cell membranes (WO 07/126365).

Surprisingly, the present inventors have now been able to prove that the same antisecretory factors can intervene in the above described biological activation of transmembrane proteins, e.g. NKCC1 through FAK and CAP, and can thus directly regulate the pathological activity of the ion channel in pathological and/or perturbed cells, effectively normalizing the intracellular pressure and transmembrane protein function in said cell, and thus allowing an improved uptake of drugs used in e.g. cancer therapy.

SUMMARY OF THE PRESENT INVENTION

The present invention relates to the use of a pharmaceutical composition comprising an antisecretory factor (AF) protein, a homologue, derivative, peptide and/or fragment thereof, having antisecretory and/or equivalent functional and/or analogue activity, preferably being selected from an antisecretory factor (AF) protein consisting of a sequence according to the following formula

X1-V—C—X2-X3-K—X4-R—X5, wherein X1 is I, amino acids 1-35 of SEQ ID NO 6, or is absent, X2 is H, R or K, X3 is S or L, X4 is T or A, X5 is amino acids 43-46, 43-51, 43-80 or 43-163 of SEQ ID NO 6, or is absent, or a modification thereof not altering the function of the polypeptide, or a pharmaceutically active salt thereof, for the manufacture of a pharmaceutical composition for optimizing delivery and/or cellular uptake of a second or further pharmaceutical substance and/or formulation.

Typically, said second or further pharmaceutical substance and/or formulation comprises an anticancer drug, radiation therapy, antibiotic substance, antiviral substance, and/or a drug targeting posttraumatic injury, neurodegeneration, a parasite, or an inflammatory condition.

The present invention in another equally preferred aspect also relates to the use of an antisecretory factor (AF) protein, peptide, derivative, homologue, and/or fragment thereof, having equivalent functional activity, and/or a pharmaceutically active salt thereof, for optimizing delivery and cellular uptake of a gene delivery.

In general, the present invention relates to the surprising insight that antisecretory factor (AF) in particular can intervene in the biological activation of transmembrane proteins, such as NKCC1 by interacting with CAP/ponsin (c-Cbl associated protein) and/or FAK (focal adhesion kinase).

AF has prior been known to co-localize with flotillin 1 and 2, a protein that is anchoraged in the lipid raft of the cell membrane and which binds to actin and to CAP, which in turn binds to the SHP-2/PTPD1 domain and SH3 of FAK in its unphosphorylated form. The present invention for the first time shows that AF can actively regulate the interaction of CAP and FAK with NKCC1, giving rise to the occurrence of uncoupled phosphorylated FAK. By uncoupling FAK from the NKCC1 complex, the ion channel is effectively shut down. The present inventors for the first time demonstrate strong evidence that AF can regulate the binding of CAP to flotillin 1 and 2, and to the SHP-2/PTPD1 domain of FAK and can potentially interfere with the oligomerization of flotillin 1 and 2 and its binding to the lipid raft in the cell membrane. AF is further by the present inventors for the first time shown to actively interfere with protein phosphatases.

Through the above described biological action, AF can effectively monitor and/or normalize abnormal function of transmembrane proteins, such as the NKCC1 ion channel in the cell membrane.

In a healthy cell, the NKCC1/FAK/CAP complex shows a natural equilibrium between phosphorylated and unphosphorylated state, thus several intracellular and extracellular effectors, such as receptors and osmotic pressure, can come to play and contribute to the finely tuned control of the state of the ion channel.

In pathological and/or perturbed cells, the finely tuned control of the state of the ion channel NKCC1/FAK/CAP complex is disturbed and the ion channel is constantly activated. Thus, the intracellular pressure of e.g. transformed cells is often higher than that of healthy cells. In pathological cells, FAK is constantly dephosphorylated and bound to the NKCC1 complex. Due to its unique potential to monitor FAK in the NKCC1 complex, whereby FAK becomes phosphorylated, AF can effectively normalize the intracellular pressure in the pathological cell, and thus potentially allow improved cellular uptake of a pharmaceutical substance, such as drugs used in e.g. cancer therapy. Consequently, normalizing the intracellular pressure in the pathological cell can in turn also contribute to normalizing the interstitial pressure in a pathological tissue. It ought to be stressed that abnormal intracellular levels of ions results in occurrent transfer of water through e.g. aquaporins (water channels).

A well known drawback in the pharmacological treatment of a broad variety of disease is the necessity to increase the dosage above optimum of the pharmaceutical substance administered to the patient due to the lack of an effective uptake of it by the pathological cells. The present invention makes it possible to utilize a proven non-toxic, biodegradable, endogenous small substance to normalize the intracellular pressure in the pathological cell, and thus potentially to allow improved cellular uptake of any pharmaceutical substance, which in turn minimizes the risk for severe side effects due to administering an over-dose of said active further component.

Furthermore, the antisecretory factor (AF) has been proven to have no adversary effect on healthy normal cells, but only to exert its normalizing effect on pathological cells. On the contrary, the administration of antisecretory factor (AF) protein, a homologue, derivative, and/or fragment thereof, having antisecretory and/or equivalent functional and/or analogue activity, or a pharmaceutically active salt thereof can instead potentially even assist healthy cells in the close vicinity of the pathological and/or perturbed cells to acquire an optimized equilibrium between phosphorylated and unphosphorylated states of NKCC1/FAK/CAP complex.

What is more, it is known since many years that a specific diet including a certain amount of malted cereals will induce the body's own endogenous production of and/or activation of antisecretory factors in the patient's blood. Thus, it is potentially possible to induce a similar normalization of the intracellular pressure in the pathological cell, and/or the Interstitial pressure in a pathological tissue, by simply feeding the patients, which are to be treated with a certain substance or to be subjected to a certain treatment, with such foodstuff as described in e.g. WO 1998/21978 or in WO 05/030246 before, during and/or after the treatment. Thus effectively and cheap improve the cellular uptake of a pharmaceutical substance, such as an anticancer drug, radiation therapy, an antibiotic substance, an antiviral substance or a drug targeting posttraumatic injury, neurodegeneration, a parasite, or an inflammatory condition.

The present invention further of course also relates to the use of the above described surprising insight that antisecretory factor (AF) can intervene in the biological activation of transmembrane proteins, such as ion channels, in particular NKCC1 through FAK in a broad variety of methods for improved drug design, for screening for and/or evaluating potential AF inhibitory and/or enhancing substances, and for evaluating efficacy and/or verifying functional activity of new or known antisecretory factor (AF) proteins, peptides, derivatives, homologues, and/or fragments thereof, having equivalent functional activity, and/or a pharmaceutically active salt thereof.

For example, phosphorylated FAK is easily distinguishable from unphosphorylated FAK by specific and commercially available antibodies. As elegantly demonstrate by the present inventors, untreated MATB cells (AtCC N.: CRL-1666, designation 13762 MATB 111) in culture show clear labeling for phosphorylated FAK. When they were exposed to a hypertonic solution, which activated the cellular NKCC1 channel, the level of phosphorylated FAK was markedly reduced, i.e. NKCC1 was activated and the cells were swelling. In starch contrast hereto, treatment with AF not only restored, but clearly induced a markedly higher level of phosphorylated FAK in the cultured cells, i.e. NKCC1 was turned off and the cells size became normalized.

Standard methods for improved drug design, for screening for and/or evaluating potential AF inhibitory and/or enhancing substances, and for evaluating efficacy and/or verifying functional activity of new or known antisecretory factor (AF) proteins, peptides, derivatives, homologues, and/or fragments thereof, having equivalent functional activity, and/or a pharmaceutically active salt thereof are well known in the art, some of which are further described in the detailed section of this application.

In another aspect, the present invention also relates to the use of a pharmaceutical composition comprising an antisecretory factor (AF) protein, a homologue, derivative, and/or fragment thereof, having equivalent functional activity, or a pharmaceutically active salt thereof, for the manufacture of a pharmaceutical composition for the treatment and/or prevention of various medical conditions selected from the group consisting of medical conditions related to cancer, tumors or tumor related conditions, infections, inflammations, posttraumatic brain injury, neurodegeneration, and parasites.

In yet another aspect, the present invention relates to the use of the newfound insight of AF's biological cellular function for the design of a new and reliable diagnostic and/or prognostic tool for monitoring and/or verifying and/or enhancing the therapeutic control of a malignant tumor in a subject suffering from a neoplastic disease, such as cancer.

In a preferred embodiment, said antisecretory factor (AF) protein, to be used according to the present invention, consists of a sequence according to the following formula

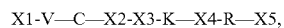

wherein X1 is I, amino acids 1-35 of SEQ ID NO 6, or is absent, X2 is H, R or K, X3 is S or L, X4 is T or A, X5 is amino acids 43-46, 43-51, 43-80 or 43-163 of SEQ ID NO 6, or is absent, or a modification thereof not altering the function of the polypeptide or peptide.

The invention is also related to various administration doses and routes suitable for the intended purpose of treatment as well as the patient's age, gender, condition etc.

FIGURE LEGENDS

FIG. 1: Cytometric assay of free floating MATBIII tumor subjected to stress and AD treatment.

The FACS analyses, 10,000 cells, demonstrated a median FSC-height of 620 in vial no. 1 (control), 450 in vial no. 2 (hypertonic NaCl 5 min), 514 in vial no. 3 (Hypertonic NaCl+AF-16, 60 min) and 576 in vial no. 4 (hypertonic NaCl+PBS, 60 min).

Figure 2:
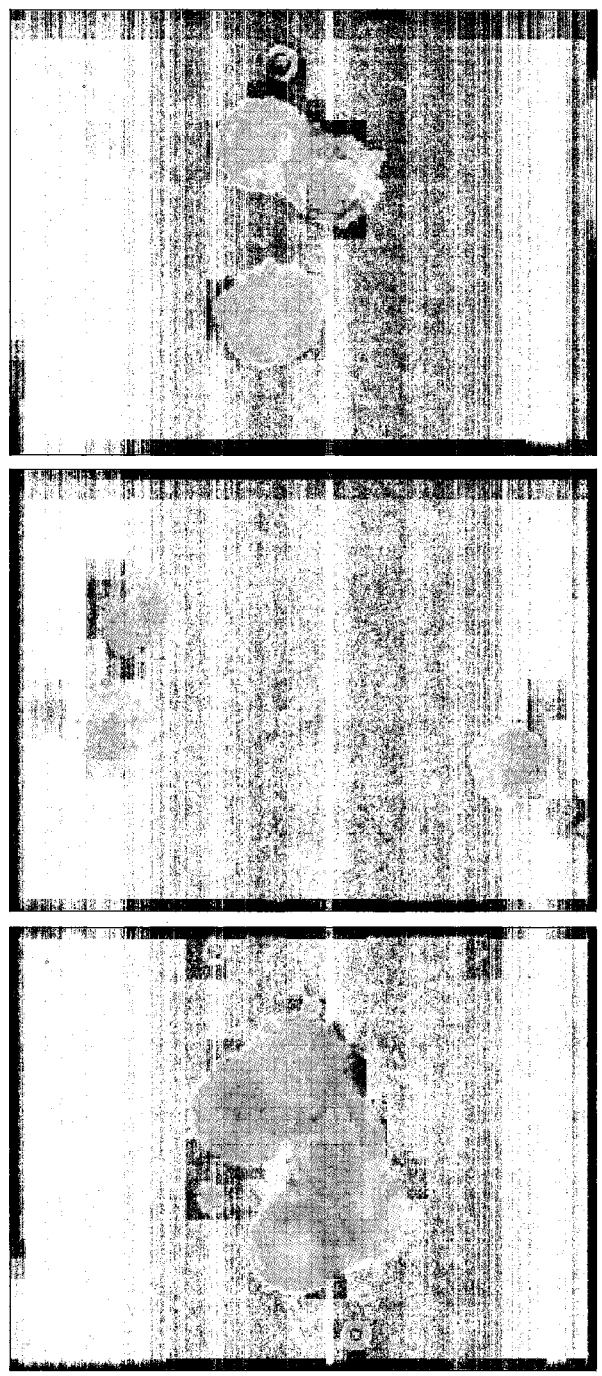

FIG. 2: Immunohistochemistry performed by means of antibodies to phosphorylated antibodies to FAK demonstrated an intense red staining in the control cells (vial no 1), while the cells of vial no 4 (PBS-treated) had a significantly lower intensity. A staining intensity similar to that in the control cells were demonstrated in the cells treated with AF-(vial 3). A. Before treatment. B. Treatment with hypertonic NaCl followed by PBS. C. Treatment with hypertonic NaCl followed by AF 16.

The cells are processed to demonstrate phosphorylated FAK (pFAK), red fluorescence. Nuclei are stained blue (DAPI).

Strong staining=high level of pFAK, i.e. the NKCC1 channel is closed.

Weak staining=low level of pFAK, i.e. the NKCC1 channel is open.

Figure 3:
Figure 3:
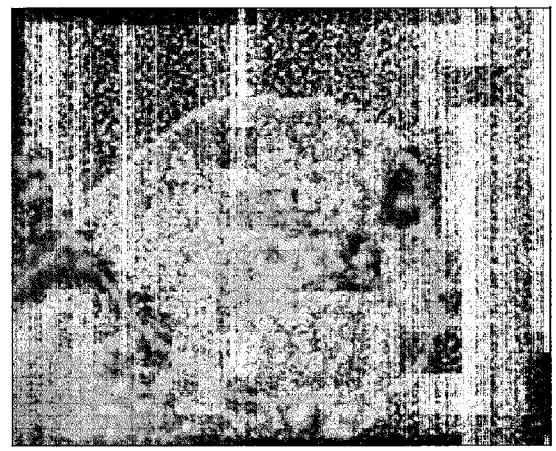
Figure 3:
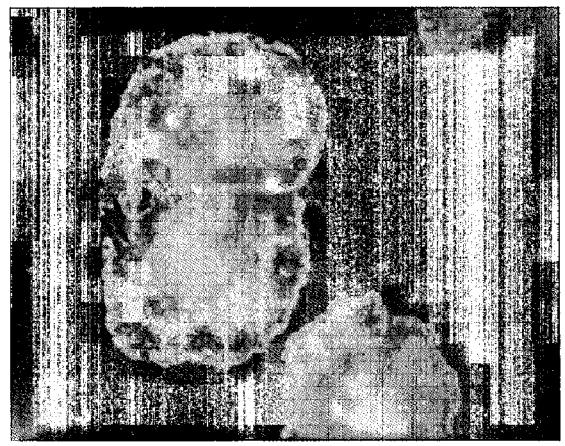

FIG. 3: GMK was cultured in on a solid surface in a series of experiments aimed to elucidate the presence and distribution of actin filaments immunohistochemically with the aid of phalloidin-FITC.

A=Untreated, normal GMK cells cultured adherent to a surface (control) and processed for demonstration of actin filaments with a phalloidin-FITC conjugate. The nucleus is stained blue.

Figure 4:
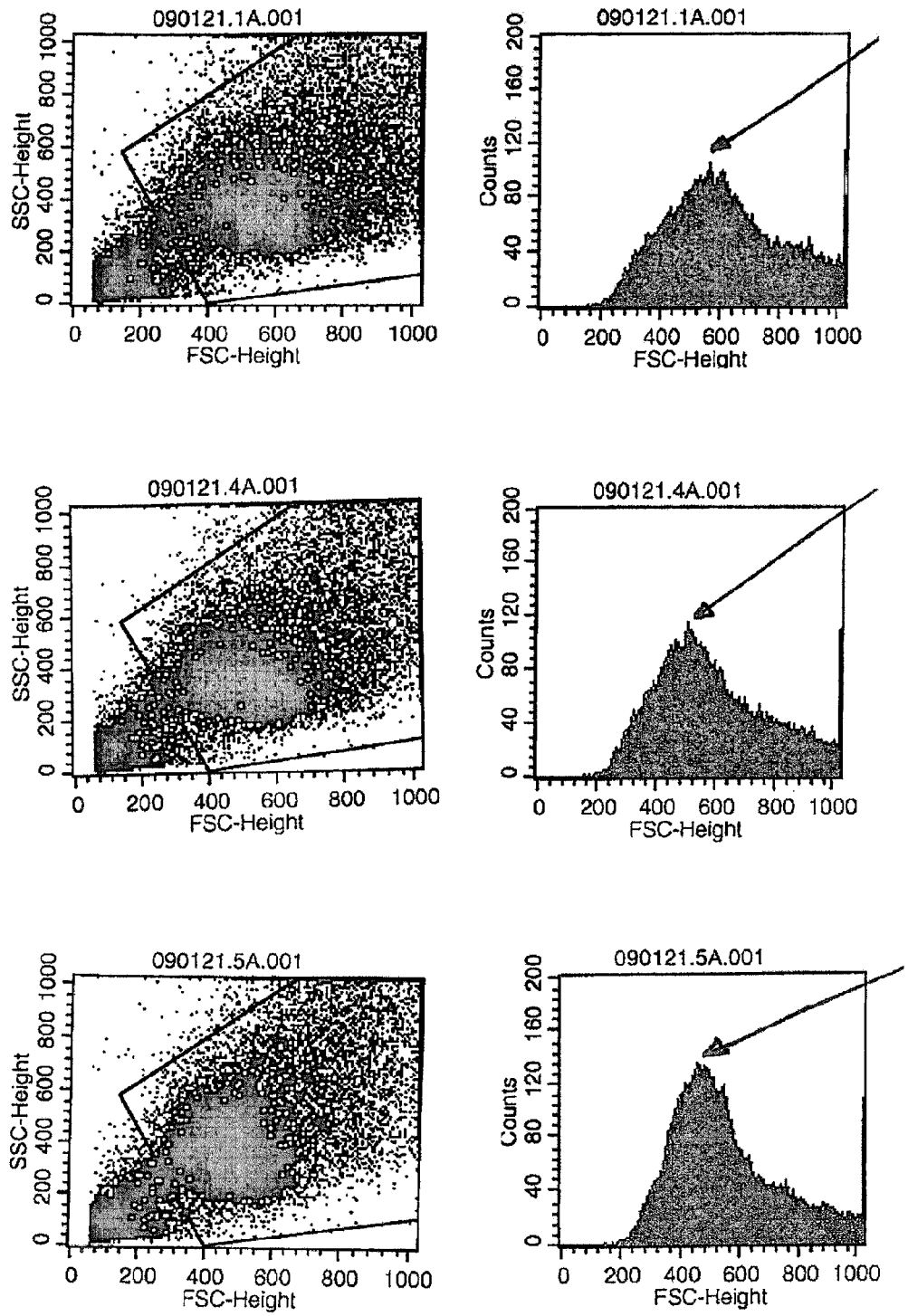

B=Treatment with cytochalasin B disintegrates the actin network and only a few clusters remain in the cytoplasm C=Concomitant treatment with cytochalasin B and AF-16 results in partial restoring of the actin network. Thus AF-16 in parts normalize the cells actin cytoskeleton FIG. 4:
A=Vial 1 control
B=Vial 4 hypertonic NaCl+vehicle, 60 min
C=Vial 3 hypertonic NaCl+AF-16, 60 min FIG. 5: Figure—Cryostat sections of MAT B III tumors cells from rats pre-treated for 60 min with either the vehicle (upper row, A-B) or AF-16 (lower row, C-D), prior to the intravenous injection of doxorubicin. The rats were killed 15 min after injection of doxyrubicin. Binding of doxorubicin to DNA results in a red fluorescence in the nuclei of cells exposed to the drug.

Only scattered nuclei are stained in tumors from rats pre-treated with the vehicle (A and B). In tumor cells from rats pre-treated with AF-16 most nuclei are stained. This shows that pre-treatment with AF-16 efficiently increases the penetration of the cytostatic drug into the tumor cells' nuclei.

Bars=100 μm

Definitions and Abbreviations

Abbreviations

IFP: interstitial fluid pressure;
PBS: phosphate buffered saline;
AF: antisecretory factor,
AF-16: a peptide composed of the amino acids VCHSKTRSNPENNVGL; octa peptide IVCHSKTR; septa peptide VCHSKTR; hexa peptide CHSKTR; penta peptide HSKTR.
FSC: Forward Scatter Count
SCS: Side Scatter Counts
SPC: Specially Processed Cereals Definitions Proteins are biological macromolecules constituted by amino acid residues linked together by peptide bonds. Proteins, as linear polymers of amino acids, are also called polypeptides. Typically, proteins have 50-800 amino acid residues and hence have molecular weights in the range of from about 6,000 to about several hundred thousand Dalton or more. Small proteins are called peptides, polypeptides, or oligopeptides. The terms "protein", "polypeptide", "oligopeptide" and "peptide" may be used interchangeably in the present context.

A "pharmaceutical composition", in the present context, refers to a composition comprising a therapeutically active amount of an antisecretory factor (AF) protein, optionally in combination with a pharmaceutically active excipient, such as a carrier or a vehicle. Said pharmaceutical composition is formulated for the appropriate route of administration, which may vary depending on the condition of the patient, as well as on other factors, such as age or preferred choice. A pharmaceutical composition comprising an antisecretory factor (AF) protein serves as a drug delivery system. The pharmaceutical composition upon administration presents the active substance to the body of a human or an animal. Said pharmaceutical composition may be in the form of e.g. tablets, pills, lozenges, capsules, stool pills, gels, solutions, etc., but is not limited thereto.

The term "pharmaceutically active salt", refers to a salt of an antisecretory factor (AF) protein, which may be any salt derived there from, based on so-called Hofmeiser's series.

Other examples of pharmaceutically active salts comprise triflouroacetate, acetate and lysine chloride, the invention is not limited thereto.

The term "antisecretory" refers in the present context to inhibiting or decreasing secretion, especially intestinal secretions. Hence, the term "antisecretory factor (AF) protein" refers to a protein capable of inhibiting or decreasing secretion in a body.

In the present context, "equivalent functional and/or analogue activity" relates to the biological effect of the antisecretory factor (AF) protein, peptide, or polypeptide, or a homologue, derivative or fragment thereof, i.e. its capacity for optimizing delivery and cellular uptake of a pharmaceutical substance and/or formulation. Standardized examples for testing and/or measuring such a capacity are well known in the field of the art. Examples are given in the experimental section of this application, such as in examples 1-6.

In the present context, an "antisecretory factor (AF) protein", or a homologue, derivative or fragment thereof, may be used interchangeably with the term "antisecretory factors" or "antisecretory factor proteins" as defined in WO 97/08202, and refers to an antisecretory factor (AF) protein or a peptide or a homologue, derivative and/or fragment thereof having antisecretory and/or equivalent functional and/or analogue activity, or to a modification thereof not altering the function of the polypeptide. Hence, it is to be understood that an "antisecretory factor", "antisecretory factor protein", "antisecretory peptide", "antisecretory fragment", or an "antisecretory factor (AF) protein" in the present context, also can refer to a derivative, homologue or fragment thereof. These terms may all be used interchangeably in the context of the present invention. Furthermore, in the present context, the term "antisecretory factor" may be abbreviated "AF". Antisecretory factor (AF) protein in the present context also refers to a protein with antisecretory properties as previously defined in WO97/08202 and WO 00/38535. Antisecretory factors have also been disclosed e.g. in WO 05/030246. Also intended by the term antisecretory factor is egg yolk enriched in antisecretory factors as disclosed in SE 900028-2 and WO 00/38535 as further described below.

A "medical food", in the present context, refers to a food or a food for special dietary use, which has been prepared with a composition with an antisecretory factor (AF) protein or alternatively has the capability to induce synthesis or activation of endogenous AF. Said food may be any suitable food, in fluid or solid form, such as a liquid or a powder, or any other suitable foodstuff. Examples of such matter may be found in WO 00/38535 or WO 91/09536. Said constituent may as well induce the uptake, formation and release of an antisecretory factor (AF) protein.

A "nebulizer", in the present context, refers to a medical device that delivers liquid medication in the form of a mist to the airways. "Nebulizer" compressors force air through tubing into a medicine cup filled with liquid medicine. The force of the air breaks the liquid into tiny mist-like particles that can be inhaled deeply into the airways.

The term "aerosol" in the present context refers to a gaseous suspension of fine solid or liquid particles.

In the present context, the term "cytostatica" is used, as well as "cytostatic drugs", "Cytostatic agents" or "cytostatic compounds", the terms are interchangeable and relate to drugs which are used in cancer therapy and are typically administered to patients undergoing chemotherapy. Cytostatic agents are substances which check the growth of pathological cells, but also of normal cells. Such substances are therefore used for the chemotherapeutical treatment of tumors, but also for post-operational treatment after removal of a tumor. Cytostatic agents can come in liquid, powder or granular form, optionally also deep-frozen. The person skilled in the art will adjust the choice and dosage of cytostatica from a plethora of cytostatica commercially available.

DETAILED DESCRIPTION OF THE INVENTION

The present invention relates to a new approach to monitor cell functions related to systems in a cell controlling the cell's dimensions and its internal milieu. An antisecretory factor (AF) protein, peptide, derivative, homologue, and/or fragment thereof, having equivalent functional activity, or a modification thereof not altering the function of the polypeptide, and/or a pharmaceutically active salt thereof, is herein used for optimizing delivery and cellular uptake of a pharmaceutical substance and/or formulation. Said pharmaceutical substance and/or formulation is in the present context selected from the group consisting of anticancer drug, anti tumor drug, radiation therapy, antibiotic substance and antiviral substance, a drug targeting posttraumatic injury, a drug targeting neurodegeneration, a drug targeting parasites, and a drug against inflammatory conditions.

In general, the present invention relates to the surprising insight that AF can be used to correct the structure and function of cells that have impaired dimensions and interior cell milieu. For example, antisecretory factor (AF) has prior been shown to be able to intervene with the cytoskeleton and its associations to lipid rafts and caveolae, filamin, galectin and flotillin complexes and is now further described to be effective in monitoring the activity of ion pumps such as NKCC1 by interacting with CAP/ponsin (c-Cbl associated protein) and FAK (focal adhesion kinase). Without wishing to be limited to a single scientific hypothesis, it is herein envisioned that AF exerts at least part of its regulating effect on NKCC1 through its previously documented influence on the cellular levels of cAMP, which in turn effects the equilibrium between phosphorylated and dephosphorylated states of a vast number of functional proteins, such as on CAP/ponsin (c-CBL associated protein) and/or FAK (focal adhesion kinase). The functionality of these proteins is consequently influenced by the levels of AF. E.g. AF's effect on the equilibrium between phosphorylated and dephosphorylated states of FAK has been demonstrated by the present inventors, and is documented in the experimental section. What is more, the present inventors have further been able to demonstrate the association of AF to a phosphatase.

As shown in the experimental section, AF-16 could be demonstrated to counteract deviations from the normal status for a cell, which gives high priority to turn normalized. The inventors thus unexpectedly demonstrated the importance of the ability of AF-16 to turn a perturbed cell normalized, as revealed for a range of cell systems tissues and organs.

AF effectively regulates and/or normalizes abnormal activity of said ion channel in perturbed and pathological cells, thereby effectively normalizing the dimensions and the intracellular pressure in the cell, which in turn also can lead to normalizing the interstitial pressure in a perturbed tissue, and thus potentially allowing an improved cellular uptake of a pharmaceutical substance, such as drugs used in e.g. cancer, inflammation and trauma therapy.

The present invention further of course also relates to the use of the above described surprising insight that antisecretory factor (AF) can intervene in the biological activation of cell systems regulating disturbed cell dimensions and internal cellular milieu through the regulation of NKCC1, by interacting with CAP/ponsin (c-Cbl associated protein) and FAK (focal adhesion kinase), in a broad variety of methods for improved drug design, for screening for and/or evaluating potential AF inhibitory and/or enhancing substances, and for evaluating efficacy and/or verifying functional activity of new or known antisecretory factor (AF) proteins, peptides, derivatives, homologues, and/or fragments thereof, having equivalent functional activity, and/or a pharmaceutically active salt thereof.

The present invention relates to the use of a pharmaceutical composition comprising an antisecretory factor (AF) protein, peptide, derivative, homologue, and/or fragment thereof, having equivalent functional activity, or a modification thereof not altering the function of the polypeptide, and/or a pharmaceutically active salt thereof, for the manufacture of a pharmaceutical composition for optimizing delivery and/or cellular uptake of a second or further pharmaceutical substance and/or formulation. Typically, said second or further pharmaceutical substance and/or formulation comprises an anticancer drug, radiation therapy, antimicrobial substance, antibiotic substance, antiviral substance and/or a drug targeting posttraumatic injury, neurodegeneration, a parasite, and/or an inflammatory condition.

In yet another aspect, the present invention relates to a pharmaceutical composition comprising an antisecretory factor (AF) protein, peptide, derivative, homologue, and/or fragment thereof, having equivalent functional activity, or a modification thereof not altering the function of the polypeptide, and/or a pharmaceutically active salt thereof in combination with a second or further pharmaceutical substance and/or formulation, wherein said second or further pharmaceutical substance and/or formulation is selected from the group consisting of an anticancer drug, radiation therapy, antibiotic substance, antiviral substance and a drug targeting posttraumatic injury, neurodegeneration, a parasite, or an inflammatory condition, as such, and to its use in medicine, in particular to its use in the treatment of the various medical indications described in the present application.

Furthermore, said pharmaceutical composition can of course comprise two or more antisecretory factor (AF) proteins, fragments or derivates, or combinations thereof, as well as further comprising a pharmaceutically acceptable excipient.

In a presently preferred embodiment, antisecretory factor (AF) proteins, peptides, derivatives, homologues, and/or fragments thereof, having equivalent functional activity, and/or a pharmaceutically active salt thereof, are shown to be able to overcome cellular barriers in malignant and/or pathological cells, and can thus be used for lowering a required drug dosage, alternatively for maximizing the dosage effect of said pharmaceutical substance and/or formulation. In consequence, said above described AF can be used to minimize toxic or unwanted side effects of said pharmaceutical substance and/or formulation.

The present invention relates to the use of a pharmaceutical composition comprising an antisecretory factor (AF) protein, a homologue, derivative, and/or fragment thereof, having antisecretory and/or equivalent functional and/or analogue activity, or a pharmaceutically active salt thereof, for the manufacture of a pharmaceutical composition for optimizing delivery and/or cellular uptake of a second or further pharmaceutical substance and/or formulation. AF and the second or further pharmaceutical substance and/or formulation can be administered together or in alternating succession. They can be co-formulated or administered in separate formulations.

As documented in experiment 1, AF-16 transiently lowers the IFP during a few hours in tumor cells, thereafter IFP returns to the original high level in 24 h. Tentatively, this time limited effect of suppressed IFP is likely to be associated with improved tumor blood circulation and metabolism, which might potentiate the efficacy of radio therapy. Thus, an increase of blood flow during radio therapy generates more free radicals and these are most effective in eliminating the malignant cells.

A presently preferred embodiment of the present invention is thus the use of a pharmaceutical composition comprising an antisecretory factor (AF) protein, a homologue, derivative, peptide and/or fragment thereof, according to the present invention, for the manufacture of a pharmaceutical composition for optimizing radiation therapy.

What is more, based on the transient and reversible nature of the lowering of the cellular IFP, the clinician can easily envision an administration routine wherein AF is administered in optimally timed intervals that are so adjusted that the IFP in the target cells are lowered just in time for the administration of the second or further pharmaceutical substance and/or formulation.

Thus, another, equally preferred embodiment relates to a method or to an administration dosage regimen for optimized delivery and/or cellular uptake of a second or further pharmaceutical substance and/or formulation, wherein said second or further pharmaceutical substance and/or formulation comprises an anticancer drug, radiation therapy, antibiotic substance, antiviral substance, and/or a drug targeting posttraumatic injury, neurodegeneration, a parasite, or an inflammatory condition.

AF and the second or further pharmaceutical substance and/or formulation can be administered together or in alternating succession. They can be co-formulated or administered in separate formulations.

In another aspect, the present invention relates to the use of a pharmaceutical composition comprising an antisecretory factor (AF) protein, a homologue, derivative, and/or fragment thereof, having equivalent functional activity, or a pharmaceutically active salt thereof, for the manufacture of a pharmaceutical composition for optimizing delivery and/or cellular uptake of a second or further pharmaceutical substance and/or formulation for the treatment and/or prevention of various medical conditions selected from the group consisting of cancer, tumor or a tumor related condition, radiation therapy, infection, posttraumatic injury, neurodegeneration, parasitic infestation, and inflammatory conditions.

The invention is also related to various administration doses and routes suitable for the intended purpose of treatment as well as the patient's age, gender, condition etc.

The pharmaceutical composition is herein formulated for intraocular, intranasal, oral, local, subcutaneous and/or systemic administration and can e.g. be formulated for administration as a spray, aerosol, and inhaler or by a nebulizer. When formulated for administration systemically to the blood said composition is preferably formulated at a dose of 0.1 µg to 10 mg per application and kg body weight and day, such as at a dose of 0.1 µg to 1 mg per application and kg body weight and day, preferably again at 1-500 µg per application and kg body weight and day, such as at 1-50 µg, or 1-100 µg per application and kg body weight and day. Such an administration can be performed either as a single dose or as multiple daily applications.

The very wide range of effective dose regimes utilized indicates that the risks for side effects and unexpected complications are minimal. Thus, the present invention will enable the treatment of excessive loads on cells and tissues as wells as to treat a patient with a wide range of doses suiting the individual response and the severity of the illness and/or the discomfort.

The pharmaceutical composition according to the present invention can in one context be administrated by application topically, locally in situ, orally, in the nose, subcutaneously and/or systemically via blood vessels or via the respiratory tract.

The present invention further of course also relates to the use of the above described surprising insight that antisecretory factor (AF) can intervene in the biological activation of NKCC1 and other transmembrane proteins through FAK in a broad variety of methods for improved drug design, for screening for and/or evaluating potential AF inhibitory and/or enhancing substances, and for evaluating efficacy and/or verifying functional activity of new or known antisecretory factor (AF) proteins, peptides, derivatives, homologues, and/or fragments thereof, having equivalent functional activity, and/or a pharmaceutically active salt thereof.

For example, phosphorylated FAK is easily distinguishable from unphosphorylated FAK by specific and commercially available antibodies. As elegantly demonstrate by the present inventors, untreated MATB cells (established breast cancer cell line) in culture show clear labeling for phosphorylated FAK. When they were exposed to a hypertonic solution, which activated the cellular NKCC1 channel, the level of phosphorylated FAK was markedly reduced, i.e. NKCC1 was activated and the cells were swelling. In starch contrast hereto, treatment with AF not only restored but clearly induced a markedly higher level of phosphorylated FAK in the cultured cells, i.e. NKCC1 was turned off and the cells' size normalized.

The present invention thus in one presently preferred embodiment relates to a method for improved drug design characterized by testing the response of cells or tissues, subject to treatment of a substance or a pharmaceutical formulation referred to in the present application and estimating the influence of AF, antisecretory factor (AF) proteins, fragments or derivates, or combinations thereof on the cellular uptake of said substance or formulation by e.g. measuring the amount of phosphorylated FAK.

In another, equally preferred embodiment, the invention relates to a method for screening for and/or evaluating potential AF inhibitory and/or enhancing substances, characterized by selecting a chemical or biological substance, exposing antisecretory factor (AF) proteins, peptides, derivatives, homologues, and/or fragments thereof, having equivalent functional activity, and/or a pharmaceutically active salt thereof to said selected substance, and subsequently testing the potential of said exposed AF to block the dephosphorylation of FAK at the NKCC1 complex by measuring the quantitative occurrence of phosphorylated FAK. In a presently specifically preferred embodiment, said testing method is performed as a high-throughput screening.

A further method is also related to herein, for evaluating the efficacy and/or verifying the functional activity of new or known antisecretory factor (AF) proteins, peptides, derivatives, homologues, and/or fragments thereof, having equivalent functional activity, and/or a pharmaceutically active salt thereof, characterized by testing the possibility of said new or known AF to block the dephosphorylation of FAK at the NKCC1 complex by measuring and quantifying the occurrence of phosphorylated FAK.

Any of the above described methods can typically alternatively be conducted in a cellular system or in a test organism. The methods are also equally applicable in in vivo, in situ, and in silico systems.

Standard Methods:
for improved drug design,
for screening for and/or evaluating potential AF inhibitory and/or enhancing substances,
for evaluating efficacy and/or verifying functional activity of new or known antisecretory factor (AF) proteins, peptides, derivatives, homologues, and/or fragments thereof, having equivalent functional activity, and/or a pharmaceutically active salt thereof, are well known in the art.

In yet another aspect, the present invention relates to the use of the newfound insight of AF's biological cellular function for the design of a new and reliable diagnostic and/or prognostic tool for monitoring and/or verifying and/or enhancing the therapeutic control of a malignant tumor in a subject suffering from cancer. In one embodiment of the present invention, antisecretory factor (AF) proteins, peptides, derivatives, homologues, and/or fragments thereof, having equivalent functional activity, are employed as markers for invasion and/or metastasis of various tumor types and/or cancer forms.

The direct regulatory effect of antisecretory factor (AF) proteins, peptides, derivatives, homologues, and/or fragments thereof, having equivalent functional activity, and/or a pharmaceutically active salt thereof on the phosphorylation state of FAK in particular, renders the said AF itself to be a potential drug candidate for cancer and/or tumor treatment.

The antisecretory factor is a class of proteins that occur naturally in the body. The human antisecretory factor protein is a 41 kDa protein, comprising 382-288 amino acids when isolated from the pituitary gland. The active site with regard to the beneficial effect on normalization of NKCC1 according to the present invention can be localized to the protein in a region close to the N-terminal of the protein, in particular localized to amino acids 1-163 of SEQ ID NO 6, more specifically to amino acid positions 35-50 on the antisecretory factor (AF) protein sequence. The biological effect being exerted by any peptide or polypeptide comprising at least 4-6 amino acids of said consensus sequence, or a modification thereof not altering the function of the polypeptide and/or peptide.

The present inventors have shown that the antisecretory factor is to some extent homologous with the protein S5a, and Rpn10, which constitutes a subunit of a constituent prevailing in all cells, the 26 S proteasome, more specifically in the 19 S/PA 700 cap. In the present invention, antisecretory factor (AF) proteins are defined as a class of homologue proteins having the same functional properties. The proteasomes have a multitude of functions related to the degradation of surplus proteins as well as short-lived unwanted, denatured, misfolded and otherwise abnormal proteins. Further, the antisecretory factor/S5a/Rpn10 is involved in the distribution and transportation of cell constituents, most evidently proteins. Antisecretory factor is also highly similar to angiocidin, another protein isoform known to bind to thrombospondin-1 and associated with cancer progression.

Homologues, derivatives and fragments of antisecretory factor (AF) proteins and/or peptides according to the present invention all have analogous biological activity of being able to be used for the manufacture of a medicament for the food for optimizing delivery and/or cellular uptake of a further pharmaceutical substance and/or formulation, as well as in a method for treating conditions such as tumors and tumor-related conditions, infections, inflammations and/or conditions caused by parasites. Homologues, derivatives and fragments, in the present context, comprise at least 4 amino acids of a naturally occurring antisecretory factor (AF) protein, which may be further modified by changing one or more amino acids in order to optimize the antisecretory factor's biological activity for optimizing delivery and/or cellular uptake of a further pharmaceutical substance and/or formulation related to the present invention, without altering the essential function of the polypeptide and/or peptide.

A fragment of an antisecretory factor (AF) protein will generally comprise the peptide/amino acid sequence or a fragment thereof in a preparation in which more than 90%, e.g. 95%, 96%, 97%, 98% or 99% of the protein in the preparation is a protein, peptide and/or fragments thereof of the invention.

Furthermore, any amino acid sequence being at least 70% identical, such as being at least 72%, 75%, 77%, 80%, 82%, 85%, 87%, 90%, 91%, 92%, 93%, 94%, 95%, 96%, 97%, 98%, or 99% identical with the amino acid sequence of a antisecretory factor (AF) protein, peptide, homologue, derivative and/or fragment according to the invention, is also considered to be inside the scope of the present invention. In the present context the terms homologous and identity are used interchangeably, i.e. an amino acid sequence having a specified degree of identity with another amino acid sequence has the same degree of homology to a specified amino acid sequence.

By a derivative is in the present context intended a protein having equivalent activity and/or a functional equivalent activity to an antisecretory factor as defined herein, being derived from another substance either directly or by modification or partial substitution, wherein one or more amino acids have been substituted by another amino acid, which amino acid can be a modified or an unnatural amino acid. For example, the antisecretory factor derivatives according to the invention may comprise an N terminal and/or a C terminal protecting group. One example of an N terminal protecting group includes acetyl. One example of a C terminal protecting group includes amide.

By proteins, homologues, derivatives, peptides and/or fragment thereof having an amino acid sequence at least, for example 95% identical to a reference amino acid sequence, is intended that the amino acid sequence of e.g. the peptide is identical to the reference sequence, except that the amino acid sequence may include up to 5 point mutations per each 100 amino acids of the reference amino acid sequence. In other words, to obtain a polypeptide having an amino acid sequence at least 95% identical to a reference amino acid sequence, up to 5% of the amino acids in the reference sequence may be deleted or substituted with another amino acid, or a number of amino acids up to 5% of the total amino acids in the reference sequence may be inserted into the reference sequence. These mutations of the reference sequence may occur at the amino or carboxy terminal positions of the reference amino acid sequence or anywhere between those terminal positions, interspersed either individually among amino acids in the reference sequence or in one or more contiguous groups within the reference sequence.

In the present invention, a local algorithm program is best suited to determine identity. Local algorithm programs, (such as Smith Waterman) compare a subsequence in one sequence with a subsequence in a second sequence, and find the combination of sub-sequences and the alignment of those sub-sequences, which yields the highest overall similarity score. Internal gaps, if allowed, are penalized. Local algorithms work well for comparing two multidomain proteins, which have a single domain, or just a binding site in common.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al, Altschul, S. F. et al (1990)). Each sequence analysis program has a default scoring matrix and default gap penalties. In general, a molecular biologist would be expected to use the default settings established by the software program used.

The antisecretory factor (AF) proteins or a peptide or a homologue, derivative and/or fragment thereof having equivalent activity as defined herein, can comprise 4 amino acids or more, such as 5-16 amino acids, such as 5, 6, 7, 8, 9, 10, 11, 12, 13, 14, 15, 16, 17, 18, 19 or 20 amino acids or more. In other preferred embodiments the antisecretory factor consists of 42, 43, 45, 46, 51, 80, 128, 129 or 163 amino acids. In preferred embodiments the antisecretory factor (AF) consists of 5, 6, 7, 8 or 16 amino acids. In another preferred embodiment, the antisecretory factor (AF) proteins or a peptide or a homologue, derivative or fragment thereof having equivalent activity according to the present invention consists of a sequence according to the following formulae:

X1-V—C—X2-X3-K—X4-R—X5 wherein X1 is I, amino acids 1-35 of SEQ ID NO 6, or is absent, X2 is H, R or K, X3 is S or L, X4 is T or A, X5 is amino acids 43-46, 43-51, 43-80 or 43-163 of SEQ ID NO 6, or is absent.

The antisecretory factor according to the present invention, can be produced in vivo or in vitro, e.g. recombinantly, synthetically and/or chemically synthesized, and/or isolated from a naturally occurring source of antisecretory factors, such as from pig pituitary glands or bird's eggs. After production, the antisecretory factors may be further processed, such as by chemical or enzymatic cleavage to smaller antisecretory active fragments or by modification of amino acids. It is presently not possible to obtain antisecretory factor (AF) protein in pure form by purification. It is however possible to produce a biologically active antisecretory factor protein recombinantly or synthetically as previously disclosed in WO 97/08202 and WO 05/030246. WO 97/08202 also discloses the production of biologically active fragments of this protein of 7-80 amino acids.

The antisecretory factor according to the invention may further comprise an N terminal and/or a C terminal protecting group. One example of an N terminal protecting group includes acetyl. One example of a C terminal protecting group includes amide.

In a preferred embodiment of the present invention the antisecretory factor is a selected among SEQ ID NO 1-6, i.e. VCHSKTRSNPENNVGL (SEQ ID NO 1, in this context also called AF-16), IVCHSKTR (SEQ ID NO 2), VCHSKTR (SEQ ID NO 3), CHSKTR (SEQ ID NO 4), HSKTR (SEQ ID NO 5), or the amino acid sequence of an antisecretory factor (AF) protein according to SEQ ID NO 6 using the common one letter abbreviations for amino acids. SEQ ID NO 1, 2, and 3 have previously been disclosed in e.g. WO 05/030246. As specified in the accompanying sequence listing, some of the amino acids in the above-specified sequences may be replaced by other amino acids. In the following in this paragraph, the position of a particular amino acid in a particular amino acid sequence is calculated from the left, denoting the most N-terminal amino acid as being in position 1 in that particular sequence. Any amino acid substitution(s) as specified below may be performed independently of any other amino acid substitution(s) in that sequence. In SEQ ID NO 1, the C in position 2 may be replaced by S, H in position 3 may be replaced with R or K, S in position 4 may be replaced with L, and/or T in position 6 may be replaced with A. In SEQ ID NO 2, C in position 3 may be replaced by S, H in position 4 may be replaced by R or K, S in position 5 may be replaced by L, and/or T in position 7 may be replaced by A. In SEQ ID NO 3, C in position 2 may be replaced by S, H in position 3 may be replaced by R or K, S in position 4 may be replaced by L, and/or T in position 6 may be replaced by A. In SEQ ID NO 4, C in position 1 may be replaced by S, H in position 2 may be replaced by R or K, S in position 3 may be replaced by L, and/or T in position 5 may be replaced by A. In SEQ ID NO 5, H in position 1 may be replaced by R or K, S in position 2 may be replaced by L, and/or T in position 4 may be replaced by A.

Also intended by the present invention is the combination of two or more of any of the fragments according to SEQ ID NO 1-6.

In one embodiment of the present invention, the pharmaceutical composition according to the invention further comprises a pharmaceutically acceptable excipient. The choice of pharmaceutically acceptable excipient and their optimum concentration for use according to the present invention can readily be determined by the skilled person by experimentation. Pharmaceutically acceptable excipients for use according to the present invention include solvents, buffering agents, preservatives, chelating agents, antioxidants, and stabilizers, emulsifying agents, suspending agents and/or diluents. The pharmaceutical compositions of the invention may be formulated according to conventional pharmaceutical practice, e.g. according to "Remington: The science and practice of pharmacy", 21st edition, ISBN 0-7817-4673-6 or "Encyclopedia of pharmaceutical technology", 2nd edition, ed. Swarbrick J., ISBN: 0-8247-2152-7. A pharmaceutically acceptable excipient is a substance that is substantially harmless to the individual to which the composition is to be administered. Such an excipient normally fulfils the requirements given by the national health authorities. Official pharmacopoeias such as e.g. the British Pharmacopoeia, the United States of America Pharmacopoeia and The European Pharmacopoeia set standards for pharmaceutically acceptable excipients.

The following is a review of relevant compositions for optional use in a pharmaceutical composition according to the invention. The review is based on the particular route of administration. However, it is appreciated that in those cases where a pharmaceutically acceptable excipient may be employed in different dosage forms or compositions, the application of a particular pharmaceutically acceptable excipient is not limited to a particular dosage form or of a particular function of the excipient. It should be emphasized that the invention is not limited to the use of the compositions mentioned in the following.

Parenteral Compositions:

For systemic application, the compositions according to the invention may contain conventional non-toxic pharmaceutically acceptable carriers and excipients, including micro spheres and liposomes.

The compositions for use according to the invention may include all kinds of solid, semi-solid and fluid compositions.

The pharmaceutically acceptable excipients may include solvents, buffering agents, preservatives, chelating agents, antioxidants, and stabilizers, emulsifying agents, suspending agents and/or diluents. Examples of the different agents are given bellow.

Example of Various Agents:

Examples of solvents include but are not limited to water, alcohols, blood, plasma, spinal fluid, ascites fluid and lymph fluid.

Examples of buffering agents include but are not limited to citric acid, acetic acid, tartaric acid, lactic acid, hydrogen phosphoric acid, bicarbonates, phosphates, diethylamide, etc.

Examples of chelating agents include but are not limited to EDTA and citric acid.

Examples of antioxidants include but are not limited to butylated hydroxyl anisole (BHA), ascorbic acid and derivatives thereof, tocopherol and derivatives thereof, cysteine, and mixtures thereof.

Examples of diluents and disintegrating agents include but are not limited to lactose, saccharose, emdex, calcium phosphates, calcium carbonate, calcium sulphate, mannitol, starches and microcrystalline cellulose.

Examples of binding agents include but are not limited to saccharose, sorbitol, gum acacia, sodium alginate, gelatine, chitosan, starches, cellulose, carboxymethylcellulose, methylcellulose, hydroxypropylcellulose, polyvinylpyrrolidone and polyethyleneglycol.

The pharmaceutical composition according to the invention is can in one context be administered locally or via intravenous peripheral infusion or via intramuscular or subcutaneous injection into the patient or via buccal, pulmonary, nasal, cutaneous or oral routes. Furthermore, it is also possible to administer the pharmaceutical composition through a surgically inserted shunt into a cerebral ventricle of the patient.

In one embodiment, the pharmaceutical composition used according to the present invention is formulated for intraocular, local, intranasal, oral, subcutaneous and/or systemic administration. In a preferred embodiment, the composition of the invention is administrated by application as a suspension or, even more preferably, a powder for inhalation with a spray, aerosol, inhaler or nebulizer nasally and/or to the respiratory tract.

The administration of a powder comprising antisecretory factors has the additional advantages in terms of stability and dosage. A pharmaceutical composition according to the invention can also be topically applied, intraocularly, intranasally, orally, subcutaneously and/or systemically administered via blood vessels. In a preferred embodiment, the pharmaceutical composition is formulated for intravenous, intramuscular, local, oral or nasal administration. Typically, when used for topical application to the eye, the applied concentration in the composition of the invention is from 1 µg to 1 mg per application, preferably 50-250 µg, either as a single dose per day or repeated several times per day (multiple doses), but is not limited thereto.

Systemically administrated to the blood, the dose is within the range of 0.1 µg to 10 mg per application and kg body weight, such as 0.1 µg to 1 mg per application and kg body weight, preferably 1-500 µg/kg body weight, preferably again 1-100 µg/kg body weight either as a single dose per day or repeated several times per day. When egg yolk enriched in antisecretory factors is used according to the present invention, this formulation is preferably administered orally.

Accordingly, the present invention relates to the use of an antisecretory factor (AF) protein or a derivative, homologue, and/or fragment thereof, having equivalent activity, and/or a pharmaceutically active salt thereof, for optimizing delivery and/or cellular uptake of a further pharmaceutical substance and/or formulation. In one embodiment, said antisecretory factor (AF) protein consists of a sequence according to the following formula

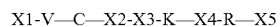

wherein X1 is I, amino acids 1-35 of SEQ ID NO 6, or is absent, X2 is H, R or K, X3 is S or L, X4 is T or A, X5 is amino acids 43-46, 43-51, 43-80 or 43-163 of SEQ ID NO 6, or is absent. In another embodiment, the invention relates to the use of an antisecretory factor (AF) protein which comprises an amino acid sequence as shown in SEQ ID NO: 1. In another embodiment, the invention relates to the use of an antisecretory factor (AF) protein which comprises an amino acid sequence as shown in SEQ ID NO: 2. In yet another embodiment, the invention relates to the use of an antisecretory factor (AF) protein which comprises an amino acid sequence as shown in SEQ ID NO: 3. In yet another embodiment, the invention relates to the use of an antisecretory factor (AF) protein which comprises an amino acid sequence as shown in SEQ ID NO: 4. In a yet further embodiment, the invention pertains to the use or an antisecretory factor (AF) protein which comprises an amino acid sequence as shown in SEQ ID NO: 5.

Furthermore, in yet another embodiment, the invention pertains to the use of an antisecretory factor (AF) protein which is a protein with an amino acid sequence as shown in SEQ ID NO 6, or a homologue, derivative and/or fragment thereof comprising amino acids 38-42 of SEQ ID NO 6.

In yet another embodiment, the invention relates to the use of a pharmaceutical composition as disclosed herein, which comprises two or more antisecretory factor (AF) proteins selected from the proteins as disclosed in SEQ ID NO: 1-6, and SEQ ID NO 6 or a homologue, derivative and/or fragment thereof comprising amino acids 38-42 of SEQ ID NO 6, or a sequence as disclosed by the general formulae described herein. Said sequences are all equally preferred to be used in the present invention.

In one embodiment of the invention, said pharmaceutical composition further comprises a pharmaceutically acceptable excipient. Such an excipient may be any preferable excipient chosen to be appropriate for the specific purpose. Examples of excipients are disclosed herein.

In another embodiment of the invention, said pharmaceutical composition is formulated for intraocular, intranasal, oral, local, subcutaneous and/or systemic administration. The chosen route of administration will vary depending on the condition of the patient to be treated and the patient's age and gender etc.

In another embodiment, the pharmaceutical composition is formulated for administration as a spray, aerosol or by a nebulizer or an inhaler. In yet another embodiment, the invention relates to a pharmaceutical composition and/or a medical food which is formulated for administration systemically to the blood at a dose of 0.1 µg to 10 mg per application and kg body weight and day, such as 0.1 µg to 1 mg per application and kg body weight and day, preferably 1-500 µg per application and kg body weight and day, preferably again 1-50 µg per application and kg body weight and day. In another embodiment, said dose is 1-1000 µg per application and kg body weight and day, such as 1-100 µg per application and kg body weight and day. The amount of the pharmaceutical composition which is distributed to the patient in need thereof will of course vary depending on the patient to be treated, and will be decided by the skilled person, such as a medical practitioner, for each occasion. Said administration can be performed either as a single dose or as multiple daily applications.

EXPERIMENTAL SECTION

Example 1

Disintegration of the Actin Filaments in Intestinal Epithelial Cells

The aim of the present experiment was to elucidate if disintegration of the actin filaments in intestinal epithelial cells (enterocytes) influenced the fluid secretion in the small intestine in adult rats.

Materials and Methods

Cholera toxin (Sigma), 3 µg, was infused in a 15 cm long ligated loop formed from the jejunum. Such a treatment resulted in 5 h in accumulation of fluid, which was measured to amount to 340 mg/cm intestinal length. The actin network, normally distinctly and strictly organized in the epithelial cells, was thoroughly disorganized. The microvilli on the luminal surface of the intestinal epithelial cells were short, clumpy and irregular in their outline while their core of microvilli almost completely lacked.

Results

If the intestinal loop was challenged with cholera toxin and then had AF-16, 100 µg, infused systemically within 10 minutes, the expected hypersecretion was abolished. The weight of the loop was roughly equal to that of the tissue after challenge with buffered balanced saline, and no fluid accumulation or inflammatory reactions could be recognized. Thus, AF-16 completely inhibited the expected fluid hypersecretion.

If on the other hand, the same amount of AF-16 was delivered 30 minutes after the cholera toxin challenge, the fluid accumulated in the loop was in the order of 320-350 mg/cm loop length. The actin network in the enterocytes, as well as in the microvilli was extensively disorganized. We conclude that there is a time window related to the hypersecretion preventing effects of AF-16 after cholera toxin challenge. These result unequivocally disclosed that AF-16 only was preventing intestinal fluid hypersecretion during the first 10 minutes to, at longest, 15 minutes, after its administration. Intestinal fluid hypersecretion is linked to the prevalence of disorganized actin network and some swelling of the enterocytes.

Combined challenge with cholera toxin and methyl-β-cyclodextrin (MβCD) of a ligated small intestine loop in rats resulted in the accumulation of 480-500 mg fluid per cm length of loop, and a prominent inflammation of the tissue. The actin filaments were extensively disorganized. MβCD is known to deplete lipid rafts of cholesterol, resulting in dissipation and aggregation of lipid raft constituents as well as abnormal functions of ion pumps and other transduction signaling receptors prevalent in these structures. The actin cytoskeleton was disorganized.

Combined challenge with cholera toxin and methyl-β-cyclodextrin (MβCD) of a ligated small intestine loop in rats followed within 10 minutes of administration of 100 µg AF-16 resulted in the accumulation of less than 100 mg fluid per cm length of loop, and no obvious inflammation of the tissue. The actin filaments were distinctly organized both in the apical parts of the intestocytes and in the almost normally appearing microvilli. We conclude that disorganization of the actin network and of the lipid rafts results in extensive fluid hypersecretion, possible to completely prevent by the administration of a sufficient single dose of AF-16, if administrated within 10-15 minutes.

Example 2

Effect of AF-16 on Tumor Cell Distribution of Doxorubicin

The effect of AF-16 on the vascular and cellular supply of a cytotoxic, low molecular weight drug in the tumor was investigated by using doxorubicin, which emits a distinct, red fluorescence and binds to DNA. The frequency of red labeled cell nuclei was used as a measure of the access of doxorubicin to and into individual tumor cells. Animals with Mat B III tumors were pretreated by either an intranasal dose of 100 µg AF-16 (n=3) or the vehicle, PBS (n=3) 60 min prior to a single i.v. injection of doxorubicin (9 mg/kg b.w). The animals were sacrificed after 15 min, the tumors were dissected out and snap frozen in liquid nitrogen. Cryostat microtome sections were prepared, attached to glass slides and fixed in 4% buffered formaldehyde. After staining nuclei with Hoechst 33342 (Sigma), the sections were mounted with Vectashield™ (Vector Laboratories Inc, USA) and examined in a Zeiss Axio10 fluorescence microscope.

Materials and Methods

Animals and tumors. Female rats of the Fisher 344 and Sprague-Dawley strains were purchased from B & K, Stockholm, Sweden. The animals were housed with a 12 h light cycle, standardized humidity and temperature, and with access to pellets and water ad libitum.

MAT B III (ATCC; CRL-1666; #13762) syngenic tumors. These tumors were established in female Fisher rats (160 gram b.w.) after a single subcutaneous injection between the shoulder blades of 106 MAT B III cells dissolved in 0.2 ml culture medium. One or more solid tumors developed in 10-12 days, and reached in 2-5 days a size of 10×8×5 mm, enabling pressure recordings.

Ethics. Permits to perform experiments were granted by the regional Animal Experiments Ethics Committee, and local and federal guidelines (EU 86/609/EEC) were followed.

Chemicals. The peptide AF-16 was synthesized and characterized by Ross Pedersen A/S, Copenhagen, Denmark. DMBA (9,10 dimethyl-1,2-benzanthracene, Hoechst 33342) and doxorubicin were purchased from Sigma. The cell culture medium RPMI 1640, supplemented with L-glutamine, was purchased from Flow Lab.

Histopathology and immunohistochemistry. At the end of the experiments the tumors were dissected, isolated free and either rapidly frozen in liquid nitrogen or fixed in 4% buffered formaldehyde. The fixed tumors were embedded in paraffin, sectioned and stained with hematoxylin and eosin.

Statistics: Results are given as means±SE. Paired design tests were used, and $p<0.05$ was considered significant.

Results

Figure 5:
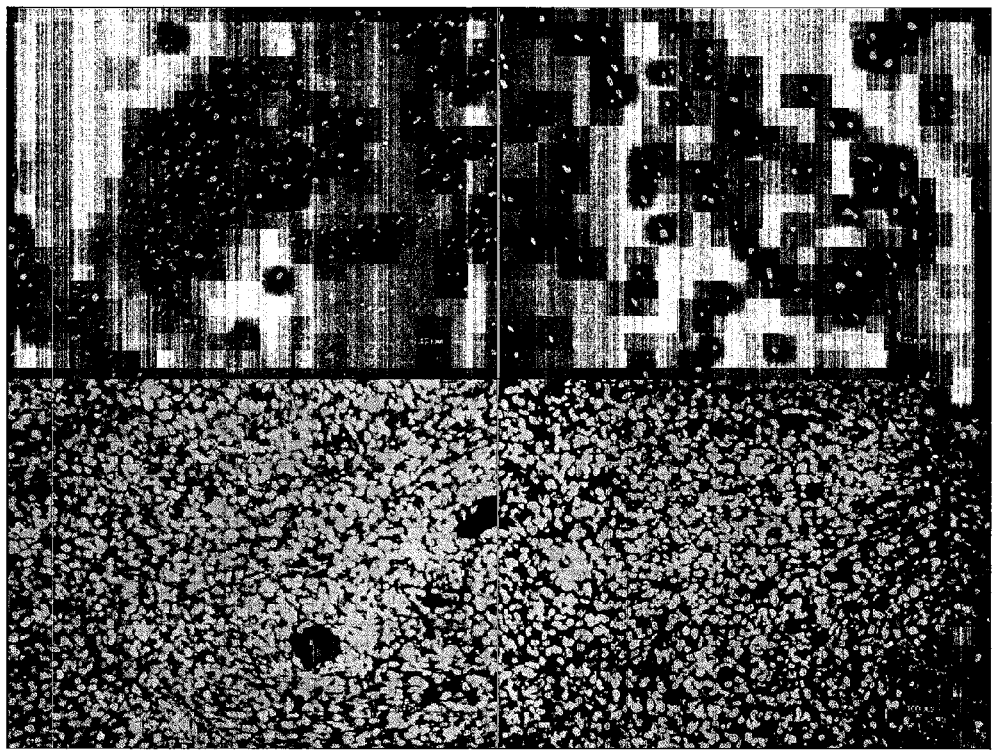

Effect of AF-16 on the distribution of doxorubicin. Doxorubicin bound to DNA can be recognized by the bright, red fluorescence of the cell nuclei. In two out of three MAT B III tumors from rats pretreated with AF-16 the frequency of positive, red nuclei was higher than in the tumors from rats pretreated with the vehicle (FIG. 5). The blue dye Hoechst 33342 stain all cell nuclei, enabling at the microscopic inspection of tumors to select areas with equal density of cells. The FIGS. 5A/B and C/D, respectively, have the same density of tumor cells, but the specimen from an animal pretreated with AF-16 display strongly increased occurrences of red nuclei. This experiment thus revealed that AF-16 enables doxorubicin to reach close to every cells at sufficient concentration. We further conclude that these results indicated that AF-16 in addition facilitates the optimized delivery and/or cellular uptake of a low molecular weight drug into the individual cells of the tumor tissue.

Example 3

The aim of these experiments was to elucidate alterations of the cell surface area, i.e. of the cell volumes, as related to the tonicity of the fluid medium in which the MATB cells were suspended. Tumor cells, as do normal cells, give high priority to maintain their cell volumes exactly regulated. The utilized strain of MATB cells is known to largely rely on the use of the fluid and ion transfer pump NKCC-1 for monitoring their dimensions and internal milieu.

Materials and Methods

The tumor cell line MATB cells (ATCC Nr: CRL-1666, designation 13762 MATB 111), a well known and commonly used cell line, was cultured in suspension and used in cell flow experiments using a FACS equipment. Thereby, the close to spherical tumor cells could rapidly alter their surface area and cell volume as a response to challenges through the extracellular fluid.

The FACS apparatus measured the MATB cells surface to be 620 units in isotonic medium, lacking any serum or other external proteins and peptide constituents that could interfere. The addition of 10% sodium chloride (NaCl) to the suspension medium resulted in 5 minutes in a shrinkage of the MATB cells surface are, to just below 500 units. That activated the NKCC-1 ion pump system as the cells sensed their dimension reductions. The FAK and the CAP systems are connected to the flotillins, linked to the actin filaments in the MATB cells. Activation of this system results in phosphorylation of NKCC-1/FAK/CAP complex, and the MATB cells ingest water and ions to swell. The cells struggle intensely and take all opportunities to regain the normal cell volume. Thereby, most evidently Na$^+$ and water enable the cell to increase its cell surface to 576 units, i.e. close to that measured at the beginning of the experiment. If, however, AF-16, 100 µg/mL, is added after 30 minutes, the activity of the NKCC-1 pump in the lipid rafts is rapidly reduced as NKCC-1 is dephosphorylated and thereby inactivated, as reflected by the cell surface of the MATB cells, which approaches 514 units. These alterations are significant as based upon more than 1000 cells per cycle.

Results

Immunohistochemical processing of MATB cells centrifuged to be deposited on glass slides confirmed the dynamics of the interaction between the CAP-FAK-NKCC-1 systems. The GMK cells had high prevalence of phosphorylated FAK in isotonic solution prior to the challenge by the addition of saline, turning the suspension medium hypertonic. The expression of phosphorylated FAK was almost completely abolished after the treatment with hypertonic solution, reflecting that the NKCC-1 ion pump with AF-16 restored the high expression of phosphorylated FAK, disclosing that the NKCC-1 pump system was shut down.

We conclude that the exposure of a suspension of MATB cells to a hypertonic solution activated the CAP-FAK system, which monitors the activity of the NKCC-1 ion pump system. Thereby, we demonstrated that AF-16 interferes with this system by controlling the activity of the NKCC-1 ion pump, by monitoring the CAP/ponsin and FAK system.

Example 5

The tumor cell line GMK was cultured in on a solid surface in a series of experiments aimed to elucidate the presence and distribution of actin filaments immunohistochemically with phalloidin-FITC.

Materials and Methods

The GMK cells were harvested after culturing to sub confluence. The cell cultures were then, in triplicate, treated according to the specifications in the following Table 1. After 30 min of treatment the cell cultures were fixed in buffered formalin and then processed for immunohistochemical demonstration of the actin pattern, as visualized with labeled phalloidin. The latter is linked with high affinity to actin filaments but not to depolymerized or G-actin. The achieved results were evaluated and photographed with the aid of a fluorescence microscope. (FIG. 3)

Results

We conclude that cytochalasin B disorganize the normal actin filament pattern in cultured, adherent GMK cells and that treatment with AF-16 to a large extent restored the normal pattern. Thus AF-16 normalized a perturbed actin cytoskeleton.

TABLE 1

| Treatment | Submembranous actin rim | Lamellipodium with actin filaments | Bundles of actin filament in cytoplasm | Dense bodies | Actin at cytocentrum | Comments |
|---|---|---|---|---|---|---|
| Control (sham treatment, Hank's) | ++ | +++ | +++ | – Not visible | + | Actin at the position of lipid rafts in plasma membrane |
| 100 µg AF-16 per mL | ++ | +++ | +++ | – | + | No change |
| 20 µM cytochalasin B during 30 min | – | – | – | ++ | +++ | Actin pattern disorganized |

TABLE 1-continued

| Treatment | Submembranous actin rim | Lamellipodium with actin filaments | Bundles of actin filament in cytoplasm | Dense bodies | Actin at cytocentrum | Comments |
|---|---|---|---|---|---|---|
| DMSO in Hank's | ++ | +++ | +++ | – | + | No change |
| 100 μg AF-16 per mL 5 min prior to 20 μM cytochalasin B added | + | – | – | ++ | ++ | Actin pattern disorganized |
| 100 μg AF-16 per mL and 20 μM cytochalasin B added concomitantly | ++ | + | + | + | ++ | Actin at plasma membrane |
| 20 μM cytochalasin B 5 min prior to the addition of AF-16 | +++ | +++ | +/++ | –/+ | + | Actin at plasma membrane |

Example 6

Effects of AF-16 on the Cellular Volumetric Regulation of MATB1 Cells In Vitro

Materials and Methods

Cell Preparation

MATB cells were cultivated according to standard procedures, and diluted to 1×106 per ml in RPMI substituted with glutamine. The cells were divided into 4 vials, designated no. 1, 2, 3 and 4. Vial 1 served as a control. To vial no. 2, 3 and 4 were added hypertonic NaCl (10 mg/ml in RPMI with glutamine), followed by addition of 50 mg of AF-16 (vial 3) or PBS (vial 4) after 30 min. Vial no 2 was subjected to FACS analyses 5 min after addition of the hypertonic NaCl solution, while the cells in vials 1, 3 and 4 were subjected to FACS analyses after a total of 60 min. Cytospin preparations were made from all vials and used for immunohistochemistry.

Results

The FACS analyses, of 10,000 cells, demonstrated a median FSC-height of 620 in vial no. (control), 450 in vial no. 2 (hypertonic NaCl 5 min), 514 in vial no. 3 (hypertonic NaCl+AF-16, 60 min) and 576 in vial no. 4 (hypertonic NaCl+PBS, 60 min) (FIG. 1). Immunohistochemistry performed by means of antibodies to phosphorylated FAK demonstrated an intense red staining in the control cells (vial no 1), while the cells of vial no 4 (PBS-treated) had a significantly lower intensity. A staining intensity similar to that in the control cells were demonstrated in the cells treated with AF-16 (vial 3)(FIG. 2).

Interpretation of the Results.

Free floating MAT B III tumor cells were used in cytometry assays, and exposed to hypertonic stress, aimed to mimic a similar situation in the solid tumor. The experimental setup was designed to elucidate if cell swelling, i.e. intracellular accumulation of fluid, contributed to the high IFP. Thus, the cells in an encapsulated tumor are considered to be inflated, maintaining this state of shape and size with a high priority by pumping fluid and ions in order to counteract influences of pH and osmotic forces.

Thus, suspended MAT B III cells were exposed to hypertonic environment, induced by adding sodium chloride to the nutrient medium. Flow cytometry disclosed a rapid decrease of the mean cell volume (FIG. 1). Within 10 min, the volume regulating system of the MAT B III cells started to regain cell volume, approaching their original cell volume after 60 min. However, the addition at 30 min after the start of the hypertonic challenge of AF-16 to the MAT BIII cells blocked the reactive increase of the cell volume. Addition of AF-16 to the cell medium did not influence the volume of the free floating MAT BIII cells if added prior to the induction of hypertonic stress (not illustrated). The lack of effect when AF-16 was added before the reactive recovery had started indicated that the fluid transfer system affected by AF-16 was temporarily inactivated until the volume recovery started. This experimental setup was repeated three times with the similar results. Taken together, these results demonstrated that AF-16 can affect the cell systems monitoring the dimensions and volume of tumor cells. No influence of AF-16 on the cell volume has been documented in vitro when tested on different normal, adult cells.

The maintenance of cells size and shape is of key importance, not only for normal cells but also for malignant ones. Cells respond rapidly when the environment is changed. Thus, the suspended MAT B III cells in the present experiment responded to a hypertonic environment by shrinkage. However, a counter reaction was rapidly started in order to restore the cells dimensions by increased uptake of fluid. However, the addition of AF-16 blocked this active cell volume expansion in an hypertonic milieu. The decrease in IFP pressure documented after AF-16 treatment could be due to an effect on the tumors cells, on the blood vessels or a combination of both. The flow cytometric results indicate that one effect could be a direct effect on the tumor cells reducing their volume and thus facilitating perfusion through the tumors. Such an effect has been demonstrated in tumors with pharmacologically induced elevated frequency of apoptosis causing a decrease of the tumor mass, which eventually resulted in an improved blood perfusion (Jain 2008). High IFP in solid tumors is often correlated to hampered penetration and uneven distribution of cytotoxic drugs. These restrictions in the drug distribution are frequently followed by a reduced anti tumor efficacy of the cytotoxic drugs.

It ought to be stressed that AF-16 transiently lowered the IFP during a few hours, thereafter IFP returned to the original high level in 24 h. Tentatively, this time limited effect of suppressed IFP is likely to be associated with improved tumor blood circulation and metabolism, which might potentiate the efficacy of radio therapy. Thus, an increase of blood flow during radio therapy generates more free radicals and these are most effective in eliminating the malignant cells.

The flow cytometry results indicated that AF-16 directly or indirectly affects essential ion and water transport systems in the tumor cells and/or in the stroma. A likely candidate could be the co-transporter NKCC-1, known to affect the volume of cells.

Addition of hypertonic NaCl induced an immediate shrinkage of the MATB cells due to altered osmotic pressure in the extracellular medium, leading to an activation of the NKCC1 pump, aiming at increasing the Na+ and water concentration into the cell, counteracting the cell shrinkage. This activation is preceded by a dephosphorylation of FAK simultaneously with a phosphorylation of NKCC1 and other transmembrane proteins. Such a dephosphorylation of FAK is inhibited by addition of AF-16. Another enzyme system, named CAP=ponsin, interacts with FAK as well as with the flotillin complex. Thus, AF-16 acts by interfering with the regulation of the balance between phosphorylation and dephosphorylation of FAK thereby changing the activity of the NKCC1 and other transmembrane proteins. AF-16 counteracts the attempts of these malignant cells to regain the cell volume and simultaneously also their intracellular pressure and dimension.

REFERENCES

1. Marks, F., Klingmüller, U., & Müller-Decker, K. Cellular signal processing. Garland, 2008.
2. Alberts, B. et al., Molecular biology of the cell. 5th edition, Garland, 2008
3. Krauss, G. Biochemistry of signal transduction and regulation. 4th edition. Wiley 2008
4. Cooper, G. M, & Hausman, R. E. The cell; a molecular approach. 4th edition. Sinauer 2007

The invention claimed is:

1. A composition comprising the amino acid sequence consisting of SEQ ID NO: 4 or a pharmaceutically acceptable salt thereof in combination with a non-peptidic low molecular weight drug which is cytotoxic or cytostatic.

2. The composition of claim 1, further comprising a pharmaceutically acceptable carrier or excipient.

3. The composition of claim 2, wherein the pharmaceutically acceptable carrier or excipient is selected from the group consisting of a solvent, a buffering agent, a preservative, a chelating agent, an antioxidant, a stabilizer, an emulsifying agent, a suspending agent, a diluent, and a disintegrating agent.

4. The composition of claim 2, wherein the pharmaceutically acceptable carrier or excipient comprises microspheres or liposomes.

5. The composition of claim 3, wherein the solvent is selected from the group consisting of water, alcohol, blood, plasma, spinal fluid, ascites fluid, and lymph fluid.

6. The composition of claim 3, wherein the buffering agent is selected from the group consisting of citric acid, acetic acid, tartaric acid, lactic acid, hydrogen phosphoric acid, bicarbonates, phosphates, and diethylamide.

7. The composition of claim 3, wherein the chelating agent is EDTA or citric acid.

8. The composition of claim 3, wherein the antioxidant is selected from the group consisting of butylated hydroxyl anisole (BHA), ascorbic acid and derivatives thereof, tocopherol and derivatives thereof, cysteine, and mixtures thereof.

9. The composition of claim 3, wherein the diluent or disintegrating agent is selected from the group consisting of lactose, saccharose, emdex, calcium phosphates, calcium carbonate, calcium sulphate, mannitol, starches, and microcrystalline cellulose.

10. The composition of claim 3, wherein the binding agent is selected from the group consisting of saccharose, sorbitol, gum acacia, sodium alginate, gelatin, chitosan, starches cellulose, carboxymethylcellulose, methylcellulose, hydroxyproplycellulose, polyvinylpyrrolidone, and polyethylene glycol.

* * * * *

SEQUENCE LISTING

```
<160> NUMBER OF SEQ ID NOS: 6

<210> SEQ ID NO 1
<211> LENGTH: 16
<212> TYPE: PRT
<213> ORGANISM: artificial sequence
<220> FEATURE:
<223> OTHER INFORMATION: Active Peptide
<220> FEATURE:
<221> NAME/KEY: VARIANT
<222> LOCATION: 6
<223> OTHER INFORMATION: may be replaced with A
<220> FEATURE:
<221> NAME/KEY: VARIANT
<222> LOCATION: 3
<223> OTHER INFORMATION: may be replaced with R or K
<220> FEATURE:
<221> NAME/KEY: VARIANT
<222> LOCATION: 4
<223> OTHER INFORMATION: may be replaced with L
<220> FEATURE:
<221> NAME/KEY: VARIANT
<222> LOCATION: 2
<223> OTHER INFORMATION: may be replaced by S

<400> SEQUENCE: 1

Val Cys His Ser Lys Thr Arg Ser Asn Pro Glu Asn Asn Val Gly Leu
  1               5                  10                  15

<210> SEQ ID NO 2
<211> LENGTH: 8
<212> TYPE: PRT
<213> ORGANISM: Artificial Sequence
<220> FEATURE:
<223> OTHER INFORMATION: Active Peptide
<220> FEATURE:
<221> NAME/KEY: VARIANT
<222> LOCATION: 7
<223> OTHER INFORMATION: may be replaced by A
<220> FEATURE:
<221> NAME/KEY: VARIANT
<222> LOCATION: 4
<223> OTHER INFORMATION: may be replaced by R or K
<220> FEATURE:
<221> NAME/KEY: VARIANT
<222> LOCATION: 5
<223> OTHER INFORMATION: may be replaced by L
<220> FEATURE:
<221> NAME/KEY: VARIANT
```

```
<222> LOCATION: 3
<223> OTHER INFORMATION: may be replaced by S

<400> SEQUENCE: 2

Ile Val Cys His Ser Lys Thr Arg
 1               5

<210> SEQ ID NO 3
<211> LENGTH: 7
<212> TYPE: PRT
<213> ORGANISM: Artificial sequence
<220> FEATURE:
<223> OTHER INFORMATION: Active Peptide
<220> FEATURE:
<221> NAME/KEY: VARIANT
<222> LOCATION: 6
<223> OTHER INFORMATION: may be replaced by A
<220> FEATURE:
<221> NAME/KEY: VARIANT
<222> LOCATION: 3
<223> OTHER INFORMATION: may be replaced by R or K
<220> FEATURE:
<221> NAME/KEY: VARIANT
<222> LOCATION: 4
<223> OTHER INFORMATION: may be replaced by L
<220> FEATURE:
<221> NAME/KEY: VARIANT
<222> LOCATION: 2
<223> OTHER INFORMATION: may be replaced by S

<400> SEQUENCE: 3

Val Cys His Ser Lys Thr Arg
 1               5

<210> SEQ ID NO 4
<211> LENGTH: 6
<212> TYPE: PRT
<213> ORGANISM: Artificial sequence
<220> FEATURE:
<223> OTHER INFORMATION: Active Peptide
<220> FEATURE:
<221> NAME/KEY: VARIANT
<222> LOCATION: 5
<223> OTHER INFORMATION: may be replaced by A
<220> FEATURE:
<221> NAME/KEY: VARIANT
<222> LOCATION: 2
<223> OTHER INFORMATION: may be replaced by R or K
<220> FEATURE:
<221> NAME/KEY: VARIANT
<222> LOCATION: 3
<223> OTHER INFORMATION: may be replaced by L
<220> FEATURE:
<221> NAME/KEY: VARIANT
<222> LOCATION: 1
<223> OTHER INFORMATION: may be replaced by S

<400> SEQUENCE: 4

Cys His Ser Lys Thr Arg
 1               5

<210> SEQ ID NO 5
<211> LENGTH: 5
<212> TYPE: PRT
<213> ORGANISM: Artificial sequence
<220> FEATURE:
<223> OTHER INFORMATION: Active Peptide
<220> FEATURE:
<221> NAME/KEY: VARIANT
<222> LOCATION: 1
<223> OTHER INFORMATION: may be replaced by R or K
<220> FEATURE:
<221> NAME/KEY: VARIANT
```

```
<222> LOCATION: 2
<223> OTHER INFORMATION: may be replaced by L
<220> FEATURE:
<221> NAME/KEY: VARIANT
<222> LOCATION: 4
<223> OTHER INFORMATION: may be replaced by A

<400> SEQUENCE: 5

His Ser Lys Thr Arg
 1               5

<210> SEQ ID NO 6
<211> LENGTH: 382
<212> TYPE: PRT
<213> ORGANISM: homo sapiens

<400> SEQUENCE: 6
```

Met Val Leu Glu Ser Thr Met Val Cys Val Asp Asn Ser Glu Tyr Met
 1               5                  10                  15

Arg Asn Gly Asp Phe Leu Pro Thr Arg Leu Gln Ala Gln Gln Asp Ala
            20                  25                  30

Val Asn Ile Val Cys His Ser Lys Thr Arg Ser Asn Pro Glu Asn Asn
        35                  40                  45

Val Gly Leu Ile Thr Leu Ala Asn Asp Cys Glu Val Leu Thr Thr Leu
50                  55                  60

Thr Pro Asp Thr Gly Arg Ile Leu Ser Lys Leu His Thr Val Gln Pro
65                  70                  75                  80

Lys Gly Lys Ile Thr Phe Cys Thr Gly Ile Arg Val Ala His Leu Ala
                85                  90                  95

Leu Lys His Arg Gln Gly Lys Asn His Lys Met Arg Ile Ile Ala Phe
            100                 105                 110

Val Gly Ser Pro Val Glu Asp Asn Glu Lys Asp Leu Val Lys Leu Ala
        115                 120                 125

Lys Arg Leu Lys Lys Glu Lys Val Asn Val Asp Ile Ile Asn Phe Gly
130                 135                 140

Glu Glu Glu Val Asn Thr Glu Lys Leu Thr Ala Phe Val Asn Thr Leu
145                 150                 155                 160

Asn Gly Lys Asp Gly Thr Gly Ser His Leu Val Thr Val Pro Pro Gly
                165                 170                 175

Pro Ser Leu Ala Asp Ala Leu Ile Ser Ser Pro Ile Leu Ala Gly Glu
            180                 185                 190

Gly Gly Ala Met Leu Gly Leu Gly Ala Ser Asp Phe Glu Phe Gly Val
        195                 200                 205

Asp Pro Ser Ala Asp Pro Glu Leu Ala Leu Ala Leu Arg Val Ser Met
210                 215                 220

Glu Glu Gln Arg His Ala Gly Gly Gly Ala Arg Arg Ala Ala Arg Ala
225                 230                 235                 240

Ser Ala Ala Glu Ala Gly Ile Ala Thr Thr Gly Thr Glu Asp Ser Asp
                245                 250                 255

Asp Ala Leu Leu Lys Met Thr Ile Ser Gln Gln Glu Phe Gly Arg Thr
            260                 265                 270

Gly Leu Pro Asp Leu Ser Ser Met Thr Glu Glu Glu Gln Ile Ala Tyr
        275                 280                 285

Ala Met Gln Met Ser Leu Gln Gly Ala Glu Phe Gly Gln Ala Glu Ser
        290                 295                 300

Ala Asp Ile Asp Ala Ser Ser Ala Met Asp Thr Ser Glu Pro Ala Lys
305                 310                 315                 320

```
Glu Glu Asp Asp Tyr Asp Val Met Gln Asp Pro Glu Phe Leu Gln Ser
            325             330             335

Val Leu Glu Asn Leu Pro Gly Val Asp Pro Asn Asn Glu Ala Ile Arg
            340             345             350

Asn Ala Met Gly Ser Leu Pro Pro Arg Pro Pro Arg Thr Ala Arg Arg
        355             360             365

Thr Arg Arg Arg Lys Thr Arg Ser Glu Thr Gly Gly Lys Gly
    370             375             380
```